US006051711A

United States Patent [19]

Tropper et al.

[11] Patent Number: 6,051,711

[45] Date of Patent: Apr. 18, 2000

[54] SYNTHESIS OF SWAINSONINE SALTS

[75] Inventors: Francois Tropper; Rajan N. Shah; Pradeep Sharma, all of Ontario, Canada

[73] Assignee: GLYCODesign Inc., Ontario, Canada

[21] Appl. No.: 09/188,164

[22] Filed: Oct. 23, 1998

Related U.S. Application Data

[60] Provisional application No. 60/098,560, Oct. 24, 1997.

[51] Int. Cl.[7] .................... C07D 491/056; C07D 317/10

[52] U.S. Cl. ............................ 546/90; 549/451; 549/454

[58] Field of Search .............................. 546/90; 549/451, 549/454, 306, 435; 548/453

[56] References Cited

U.S. PATENT DOCUMENTS

| | | | |
|---|---|---|---|
| 3,274,202 | 9/1966 | Mohrbacher | 260/294 |
| 4,792,558 | 12/1988 | Sunkara et al. | 514/299 |
| 4,837,237 | 6/1989 | Rohrschneider et al. | 514/62 |
| 4,857,315 | 8/1989 | Dennis | 424/85.2 |
| 4,894,388 | 1/1990 | Fleet | 574/425 |
| 4,996,329 | 2/1991 | Fleet et al. | 548/453 |
| 5,021,427 | 6/1991 | Elbein et al. | 514/315 |
| 5,023,340 | 6/1991 | Fleet | 548/453 |
| 5,041,555 | 8/1991 | Fleet et al. | 548/541 |
| 5,075,448 | 12/1991 | Fleet | 546/112 |
| 5,075,457 | 12/1991 | Fleet | 548/453 |
| 5,187,279 | 2/1993 | Cha et al. | 546/183 |
| 5,264,356 | 11/1993 | Rohrschneider | 435/238 |
| 5,272,070 | 12/1993 | Lehrman et al. | 435/172.1 |
| 5,288,875 | 2/1994 | Cha et al. | 548/453 |
| 5,376,675 | 12/1994 | Alphey et al. | 514/425 |
| 5,382,709 | 1/1995 | Farr et al. | 568/704 |
| 5,438,069 | 8/1995 | Farr et al. | 514/1 |
| 5,466,809 | 11/1995 | Dime | 546/183 |
| 5,484,925 | 1/1996 | Cha et al. | 546/90 |
| 5,621,106 | 4/1997 | Dime | 546/183 |
| 5,633,261 | 5/1997 | Dime | 514/299 |
| 5,650,413 | 7/1997 | Carver et al. | 514/299 |
| 5,780,633 | 7/1998 | Okada et al. | 546/112 |

FOREIGN PATENT DOCUMENTS

| | | |
|---|---|---|
| 2040058 | 10/1991 | Canada . |
| 1298549 | 4/1992 | Canada . |
| 0004260 | 10/1979 | European Pat. Off. . |
| 0036269 | 9/1981 | European Pat. Off. . |
| 104826 | 4/1984 | European Pat. Off. . |
| 295538 | 12/1988 | European Pat. Off. . |
| 424349 | 4/1991 | European Pat. Off. . |
| 451834 | 10/1991 | European Pat. Off. . |
| 3507019 | 8/1986 | Germany . |
| 60-218389 | 4/1984 | Japan . |
| 60-166680 | 8/1985 | Japan . |
| 60-193986 | 10/1985 | Japan . |
| 61-227566 | 9/1986 | Japan . |
| 61-277685 | 12/1986 | Japan . |
| WO9006311 | 6/1990 | WIPO . |
| WO93/05040 | 3/1993 | WIPO . |
| WO93/05781 | 4/1993 | WIPO . |
| WO9309117 | 5/1993 | WIPO . |
| WO9535094 | 12/1995 | WIPO . |
| WO9640683 | 12/1996 | WIPO . |
| WO98/14445 | 4/1998 | WIPO . |
| WO98/14446 | 4/1998 | WIPO . |

OTHER PUBLICATIONS

Pearson, W. H. and E.J. Hembre, J. Org. Chem. 61:5546–5556, 1996.

Rodriguez, R. and F. Bermejo, Tetrahedron Letters 37: 5581–5584, 1996.

Keck, G. E. and D.R. Romer, J. Org. Chem. 58: 6083–6089, 1993.

Kim Y.G., and J.K. Cha, Tetrahedron Letters, 30:5721–5724, 1989.

Tadano, K. et al, J. Org Chem,. 53:5209–5215, 1988.

Tadano, K., et al, Bull Chem. Soc. Jpn. 59: 3885–3892, 1986.

Tadano, K., et al, Bull. Chem. Soc. Jpn., 60: 3667–3671, 1987.

Honda, T. et al, Chem. Soc. Perkin Trans. 1, p. 2091, 1994.

Suami, T. et al, Chemistry Letters, pp. 513–516, 1984.

Hembre, E.J. and W. H. Pearson, Tetrahedron 53: 11021–11032, 1997.

Fleet, G.W.J. et al., Tetrahedron Letters 26: 3127–3130, 1985.

Fleet, G.W.J. et al, Tetrahedron 44:2649, 1988.

Bennett R.B. et al, J. Am. Chem. Soc. 111:2580–2582, 1989.

W.H. Pearson and Hembre, E.J., J. Org. Chem. 1996, 61:7217–7221.

Carpenter, N.M. et al Tet. Lett. 1989, 30:7261–7264.

Miller, S.A. et al, J. Am. Soc. 1990, 112:8100–8112.

Cohen, N. et al, J. Am. Chem. Soc. 1983, 105:3661–3672.

Cohen, N. et al, Org. Synth. (1985) 63: 127–135.

R.H. Furneaux et al., The Chemistry of Castanospermine, Part IV:Synthetic Modifications at C–8, Tetrahedron, 1995, 51: 12611–12630.

(List continued on next page.)

*Primary Examiner*—John Kight

*Assistant Examiner*—Charanjit S. Aulakh

[57] ABSTRACT

A method for synthesizing swainsonine salts and intermediates thereof comprising subjecting a compound of the formula I

I

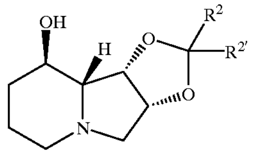

wherein $R^2$ and $R^{2'}$ are the same or different and represent alkyl, halogen, alkenyl, alkoxy, cycloalkyl or aryl which may be substituted, to acid hydrolysis in the presence of a $C_{1-4}$ alkanol to obtain a crystalline salt of swainsonine; and optionally, recrystallizing the swainsonine salt from a $C_{1-4}$ alkanol. The reaction may be used in combination with one or more additional reaction steps.

53 Claims, No Drawings

OTHER PUBLICATIONS

Takahata, M. et al, The Alkaloids, vol. 44, Academic Press, New York (1993) at 189.
Aoyama, H. et al, J. Org. Chem. 57: 3037–3041, 1992.
S.R. Wilson and R.A. Sawicki J. Org. Chem 44:330, 1979.
Villiani et al, J. Org. Chem., 6:142, 1962.
Hibbett, E. P., and J. Sam, J. Het. Chem. 7:857,1970.
Heidt, P.C. et al, Tetrahedron Letters 31: 5441, 1990.
Reinecke, M., and L.R. Kray, J. Org. Chem. 29: 1736, 1964.
Chastanet, J. and G. Roussi, J. Org, Chem, 50:2910–2914, 1985.
Bashyal, B.P. et al, Tetrahedron Letters, 3083,1987.
Clemo, G.R. and T.P. Metcalfe, J. Chem. Soc. 1937, p. 1518.
Leonard, N.J. et al, J. Org. Chem. 22:1445, 1957.
Winkler D.A. and G. Holan, J. Med. Chem., 32: 2084, 1989.
Reinecke, M.G. and L.R. Kray, J. Org. Chem 30:3671, 1965.
Bogeso, K.P. et al, J. Med. Chem. 30:142–150, 1987.
Austin, G.N. et al, Tetrahedron, 43:3095–3108, 1987.
Hino e al, J. Antibiot. (Tokyo) 38: 926–935, 1985.
Skelton, B.W. and White, A.H., Aust. J. Chem. 33:435–9, 1980.
Holden R.T. and R. Raper, J. Chem. Soc. p. 2545, 1963.
Biniecki, S. et al., Chemical Abstracts, 1984, 101, No. 90743a.
Biniecki, S. et al., Chemical Abstracts, 106, 1987, 138204h.
Boegesoe, K. P., et al., Chemical Abstracts, 106, 1987, No. 84369v.
Smith, M.B. et al., Chemical Abstracts vol. 104, 1986, No. 51007f.
Hashimoto, S. et al., Chemical Abstracts vol. 106, 1987, No. 138253y.
Miyano, Se. et al, Chemical Abstracts, vol. 98, 1983, No. 179148c.
Yoon, U.C. et al., Chemical Abstracts vol. 97, 1982, No. 38827r.
Fujiwara, et al, Chemical Abstracts vol. 117, 1992, No. 211862e.
Winterfield, K. et al., Chemical Abstracts vol. 74, 1971, No. 3456s.
Motohiro, et al., Chemical Abstracts, vol. 101, Abstract 28283x, 1984.
Temple, Jr. C. and G. Rener, J Med Chem 32:2089, 1989.
Nicolson, G.L. Biochem Biophys. Acta. 695:113, 1982.
Tulsiani, D.R.P. et al., Archives Biochem. Biophys. 232: 76–85, 1984.
Oredipe, O.A., et al, J. National Cancer Institute, 83:1149, 1991.
Bowlin, T. L. et al., Cancer Research 49:4109–4113, 1989.
Tulsiani, D.R.P. and O. Touster, J. Biol. Chem., 258: 7578–7585, 1983.
J.W. Dennis, et al, Biochemical Pharmacology 46:1459, 1993.
Levine, A.S. et al., Can. Res. 39: 1645–1650, 1970.
Goss P.E. et al, Cancer Res. 54: 1450, 1994.
Goss, P.E. et al, Clin. Cancer Res. 3:1077, 1997.
Dennis J. W. in "Cell Surface Carbohydrates and Cell Developement", Fukuda M.(ed)., CRC Press, Boca Raton, Ann Arbor London, 1992, Chapter 6, pp. 161–194.
Dennis J. W. et al, Science, 236:582, 1987.
VanderElst, E. and J.W. Dennis, Experimental Cell Research 192: 612–621, 1991.
J.W. Dennis, Cancer Research 46:5131, 1986.
Humphries, M.J. et al, Proc.Natl. Acad, Sci, USA, 83:1752, 1986.
Colegate S.M. et al., Aust. J. Chem. 1979, 32: 2257–64, 1979.
Molyneux R.J. an L.F. James, Science 216:190, Apr. 1982.
Schneider M.J. et al, Tetrahedron 39(1): 29, 1983.
Fernandes, B. et al, Cancer Research 51: 718, 1991.
Tulsiani D.R.P. et al, J. Biol. Chem. 257:7936, 1982.
Olden K. et al, Pharmac. Ther. 50:285, 1991.
Humphries, M.J. et al, Cancer Research 48:1410, 1988.
Demetriou M. et al, J. Cell Biol. 130:383–392, 1995.
Dennis et al., Oncogene 4:853–860, 1998.
M. Yagita and E. Sakela, Scand. J. Immunol 31:275–282, 1990.
White, S.L. et al, Biochem Biophys. Res. Commun. 150:615–625, 1988.
Seftor, R.E.B. Melanoma Research 1:43–54, 1991.
Yagel S., et al., Intl. J. Cancer 44:685, 1989.
J.W. Dennis et al, J. National Cancer Institute 81:1028, 1989.
J.W. Dennis et al, Cancer Research 50:1867, 1990.
Humphries, M.J. and K. Olden, Pharmac. Ther. 44:85–105, 1989.
White, S.L. et al., Cancer Communications, 3(30):83, 1991.

SYNTHESIS OF SWAINSONINE SALTS

This application claims priority benefit of Provisional application No. 60/098,560 filed Oct. 24, 1997.

FIELD OF THE INVENTION

The invention relates to methods for synthesizing swainsonine, and derivatives of swainsonine, and particularly salts of swainsonine.

BACKGROUND OF THE INVENTION

Swainsonine free base is an indolizidine alkaloid having biological activity, including the inhibition of many mannosidases. Syntheses of the free-base alkaloid have been described, such as (a) Pearson and Hembre, J. Org. Chem., 1996, 61:7217–7221; (b) Carpenter, N. M. et al., Tet. Lett. 1989, 30:7261–7264; (c) Bennett, R. B., III et al., J. Am. Chem. Soc., 1989, 111:2580–2582; (d) Takahata, M. et al., The Alkaloids, vol. 44 Academic Press, New York (1993), at 189; (e) Miller, S. A., et al., J. Am. Chem. Soc. 1990, 112:8100–8112; and (f) Cohen, N., et al., J. Am. Chem. Soc. 1983, 105:3661–3672. Additional syntheses are described in U.S. Pat. No. 5,187,279 (Cha) and U.S. Pat. No. 5,075,448 (Fleet). Pearson and Hembre claim to produce 4.5 g of swainsonine free base in 20% yield from the lactone intermediate (2,3-O-isopropylidene-D-erythronolactone) using a method which requires eleven steps, three chromatographic separations and four crystallizations (at 7218, column 2). According to Pearson and Hembre, as of their 1996 publication, attempts to scale up even the shortest known synthetic route had been unsuccessful (at 7217, column 1).

SUMMARY OF THE INVENTION

The invention features methods for synthesizing swainsonine its salts, and derivatives of swainsonine and their salts. Advantages of the methods of the invention include high yields, fewer chromatographic separations, fast reaction times, and less expensive reagents. The methods also feature the absence of chlorinated solvents, toxic reagents such as osmium tetraoxide, and energy-intensive cryogenic conditions. In view of the increasing interest in the products of this synthesis, the advantages provided by this method are of considerable commercial significance. The methods are particularly useful for large scale processes (e.g. 200–250 g final product scale) and to provide highly purified and stable products.

Methods of the invention have particular application in the synthesis of swainsonine salts. In particular, a disclosed method provides swainsonine hydrochloride in 20% yield from the 2,3-O-isopropylidene-D-erythronolactone intermediate.

Broadly stated the present invention relates to a method for synthesizing a salt of swainsonine comprising (i) subjecting a compound of the formula I

I

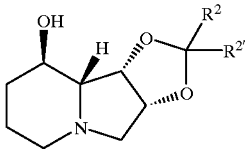

wherein $R^2$ and $R^2$ are the same or different and represent alkyl, halogen, alkenyl, alkoxy, cycloalkyl or aryl, to acid hydrolysis in the presence of a $C_{1-4}$ alkanol to obtain a crystalline salt of swainsonine; and optionally (ii) recrystallizing the swainsonine salt from a $C_{1-4}$ alkanol.

The reaction may be used in combination with one or more of the reaction steps (A) to (G) described herein.

The invention specifically contemplates methods where $R^2$ and $R^{2'}$ are the same and represent $C_{1-4}$ alkyl, or where one of $R^2$ and $R^{2'}$ represents alkyl or aryl and the other of $R^2$ and $R^{2'}$ represents alkoxy or halogen.

In an embodiment the compound of the formula I is 1,2-O-isopropylidenedioxy-8-hydroxyindolizidine (i.e. swainsonine acetonide). In a particular embodiment, the invention relates to a method for preparing an isolated and purified crystalline hydrochloride salt of swainsonine comprising converting 1,2-O-isopropylidenedioxy-8-hydroxyindolizidine (i.e. swainsonine acetonide) to a hydrochloride salt by acid hydrolysis in the presence of a $C_{1-4}$ alkanol to obtain a crystalline hydrochloride salt of swainsonine, and optionally recrystallizing the salt in a $C_{1-4}$ alkanol. The method of the invention provides a swainsonine hydrochloride preparation having a purity of greater than 95%, more preferably 98%, and most preferably 99.6%.

The invention also provides a method of preparing a swainsonine salt comprising:

(A) reacting a lactone of the formula II

II

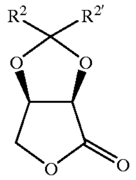

wherein $R^2$ and $R^{2'}$ are the same or different and represent alkyl, alkenyl, halogen, alkoxy, cycloalkyl, or aryl, with diisobutylalumnium hydride in an organic solvent preferably selected from the group consisting of toluene, benzene, xylene, chlorobenzene, and t-butyl methyl ether, to obtain a lactol of the formula III

III

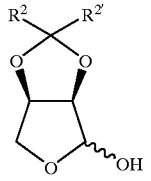

wherein $R^2$ and $R^{2'}$ are as defined above;

(B) reacting the lactol of the formula III with a phosphonium bromide salt to obtain an olefinic alcohol of the formula IV:

IV

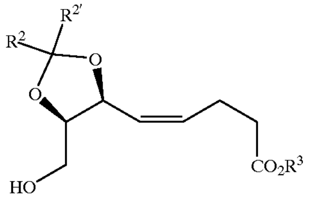

wherein $R^2$ and $R^{2'}$ are as defined above, and $R^3$ is $C_{1-10}$ alkyl or aryl;

(C) reacting the olefinic alcohol of the formula IV with a phosphine, dialkylazodicarboxylate, and azide source to obtain an azide of the formula V

V

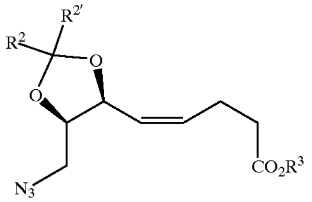

wherein $R^2$, $R^{2'}$, and $R^3$ are as defined above;

(D) refluxing the azide of the formula V in a non-reactive high boiling solvent (e.g. greater than 90° C.) preferably selected from the group consisting of toluene, benzene, xylene, chlorobenzene, and dimethyl formamide (DMF), to form an imino ester of the formula VI

VI

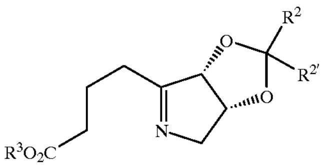

wherein $R^2$, $R^{2'}$, and $R^3$ are as defined above;

(E) reacting the imino ester of the formula VI with an alkali metal hydroxide in a mixture of water and a miscible non-reactive organic solvent (e.g. a $C_{1-4}$ alkanol or THF) and acidifying the reaction mixture to obtain an imino acid of the formula VII

VII

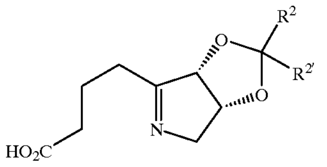

wherein $R^2$ and $R^{2'}$ are as defined above;

(F) cyclizing the imino acid of the formula VII by refluxing in an organic solvent preferably selected from the group consisting of toluene, benzene, xylene, chlorobenzene, and t-butyl methyl ether, with a catalyst, to form an enamide of the formula VIII;

VIII

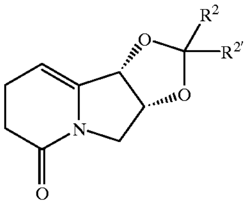

wherein $R^2$ and $R^{2'}$ are as defined above (G) reducing the enamide of the formula VIII with a borane reagent in an organic solvent preferably selected from the group consisting of toluene, hexane, benzene, xylene, chlorobenzene, blends of petroleum ether, ether, and t-butyl methyl ether, and oxidizing by peroxide the resulting alkyl borane, to obtain a protected swainsonine of the formula I;

I

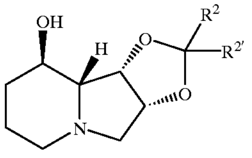

wherein $R^2$ and $R^{2'}$ are as defined above;

(H) subjecting the protected swainsonine to acid hydrolysis in the presence of a $C_{1-4}$ alkanol to obtain a crystalline swainsonine salt; and optionally (I) recrystallizing the swainsonine salt from a $C_{1-4}$ alkanol.

A method of the invention may additionally comprise converting the swainsonine salt to swainsonine, and preparing a derivative of swainsonine from the swainsonine salt or swainsonine.

The invention also provides novel methods for preparing intermediates used in the methods of the invention. The intermediates may be used in conventional processes for preparing swainsonine or derivatives thereof.

The invention also features a swainsonine salt obtained by a method including steps (C), (E), (F), or (H), or a combination thereof e.g., steps (F) to (H), steps (C), (F), and (H), steps (C) to (H), or steps (A)–(H) as described herein. This synthesis exemplifies the numerous advantages of several disclosed individual transformations of the invention, namely, steps (A) to (H), and in particular steps (C), (E), (G), (F), and (H) as described herein. The invention features the disclosed individual steps and additional combinations thereof.

The invention includes individually-improved conditions for specific transformations (e.g, steps (C), (E), (F), (G), or (H) alone), as well as advantageous combinations thereof to produce synthetic intermediates, including the free-base, in a commercially viable manner.

Using the methods of the invention isolated, highly purified, and stable preparations of salts of swainsonine, and salts of derivatives of swainsonine can be prepared. Therefore, the invention features isolated, purified, and stable salts of swainsonine, and salts of derivatives of swainsonine.

DETAILED DESCRIPTION OF THE INVENTION

The methods of the invention and the particular improvements therein can be used to synthesize swainsonine, a salt of swainsonine, or a derivative of swainsonine or a salt thereof. The methods of the invention may be particularly used to prepare halide salts of swainsonine. A "halide salt" is preferably a hydrochloride, hydrofluoride, hydrobromide, or hydroiodide salt, preferably, a hydrochloride or hydrobromide salt. The methods may be particularly useful in synthesizing crystalline salts, most preferably hydrochloride or hydrobromide crystalline salts of swainsonine. A "crystalline hydrochloride or hydrobromide salt of swainsonine" includes molecules of swainsonine hydrochloride or hydrobromide in a unit cell held together by hydrogen bond interactions. Preferably a crystalline hydrochloride or hydrobromide swainsonine salt comprising four molecules of swainsonine hydrochloride or hydrobromide in a unit cell is synthesized. Most preferably the crystalline hydrochloride or hydrobromide salt comprises four molecules of swainsonine hydrochloride or hydrobromide in a unit cell. A crystalline swainsonine hydrochloride or hydrobromide salt has space group symmetry $P2_12_12_1$. In a preferred embodiment of the invention, the crystal of the swainsonine hydrochloride or hydrobromide salt comprises orthorhombic unit cells. The unit cell for a crystal of a swainsonine hydrochloride salt may have the unit cell lengths a=8.09±0.01 Å, b=9.39±0.01 Å, and c=13.62±0.01 Å.

Derivatives of swainsonine and salts of derivatives may be prepared using the methods described herein, and the derivatives and salts prepared by the methods are contemplated in the present invention. A "derivative" of swainsonine refers to a compound that possesses a biological activity (either functional or structural) that is substantially similar to the biological activity of swainsonine. The term "derivative" is intended to include "variants" "analogs" or "chemical derivatives" of swainsonine. The term "variant"is meant to refer to a molecule substantially similar in structure and function to swainsonine or a part thereof. A molecule is "substantially similar" to swainsonine if both molecules have substantially similar structures or if both molecules possess similar biological activity. The term "analog" refers to a molecule substantially similar in function to a swainsonine molecule. The term "chemical derivative" describes a molecule that contains additional chemical moieties which are not normally a part of the base molecule.

Steps (H) and (I)

The method of the invention involves subjecting a protected swainsonine of the formula I

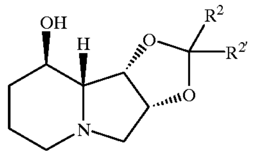

wherein $R^2$ and $R^{2'}$ are the same or different and represent alkyl, halogen, alkenyl, alkoxy, cycloalkyl, or aryl to acid hydrolysis in the presence of a $C_{1-4}$ alkanol to obtain a crystalline swainsonine salt; and optionally recrystallizing the swainsonine salt from a $C_{1-4}$ alkanol.

The invention specifically contemplates methods where $R^2$ and $R^{2'}$ are the same and represent $C_{1-4}$ alkyl, or where one of $R^2$ and $R^{2'}$ represents alkyl or aryl and the other of $R^2$ and $R^{2'}$ represents alkoxy or halogen.

A pure swainsonine salt can be produced by replacing evaporated water with a $C_{1-4}$ alkanol in a continuous or stepwise fashion. In this way, a pure swainsonine salt crystallizes out of the alkanol solution as the water concentration drops.

Hereinabove and in the following the term "alkyl", alone or in combination, refers to a branched or linear hydrocarbon radical, typically containing from 1 through 15 carbon atoms, preferably 1 through 10. Typical alkyl groups and substituted alkyl groups include but are not limited to methyl, ethyl, 1-propyl, isopropyl, 1-butyl, 2-butyl, tert-butyl, pentyl, isopentyl, hexyl, isohexyl, 2,2,2-trichloroethyl, and the like. Preferred alkyl groups are methyl ethyl, and isopropyl.

The term "alkoxy" refers to an alkyl or cycloalkyl linked to the parent molecular moiety through an oxygen atom. Examples of alkoxy groups are methoxy, ethoxy, propoxy, vinyloxy, allyloxy, butoxy, pentoxy, hexoxy, cyclopentoxy, and cyclohexoxy.

The term "alkenyl", alone or in combinations refers to an unsaturated branched or linear group typically having from 2 to 15 carbon atoms and at least one double bond. Examples of alkenyl groups and substituted alkenyl groups include but are not limited to ethenyl, 1-propenyl, 2-propenyl, 1-butenyl, 1,3-butadienyl, hexenyl, pentenyl, 1-phenylethyl, (4-methoxyphenyl)ethyl, and the like.

The term "cycloalkyl" refers to cyclic hydrocarbon groups and includes but is not limited to cyclopropyl, cyclobutyl, cyclopentyl, cyclohexyl, cycloheptyl, and cyclooctyl.

The term "halogen", alone or in combination, refers to a member of the family fluorine, chlorine, bromine, or iodine, preferably chlorine.

The term "aryl", alone or in combination, refers to a monocyclic or polycyclic group, preferably a monocyclic or bicyclic group. An aryl group may optionally be substituted as described herein. Examples of aryl groups and substituted aryl groups are phenyl, benzyl, benzyl ester, p-nitrobenzyl, p-methoxybenzyl, biphenyl, 2,4demethoxybenzyl, 3,4-dimethoxybenzyl, 2-nitrobenzyl, and naphthyl.

The term "alkylidene" used herein and used in the terms herein such as an "alkylidene-protected swainsonine" includes methylene, ethylidene, acetonide (isopropylidene), 1-t-butylidene, 1-phenylethylidene, (4-methoxyphenyl) ethylidene, 2,2,2-trichloroethylidene, cyclopentylidene, cyclohexylidene, benzylidene, p-methoxybenzylidene, 2,4-demethoxybenzylidene, 3,4-dimethoxybenxylidene, and 2-nitrobenzylidene.

One or both of $R^2$, $R^{2'}$, or $R^3$ which have available functional groups may be substituted with one or more substituents including but not limited to the following: alkyl alkoxy, alkenyl, alkynyl, or halogen.

In a preferred embodiment of the invention the compound of the formula I is 1,2-O-isopropylidenedioxy-8-hydroxyindolizidine.

The acid hydrolysis may be carried out in anhydrous or non-anhydrous conditions using hydrochloric acid, hydrofluoric acid, hydrobromic acid, hydrogen fluoride, hydrogen chloride, or hydrogen bromide. $C_{1-4}$ alkanols which may be used in the method of the invention include methanol, ethanol, propanol, isopropanol, and butanol, preferably a $C_{1-3}$ alkanol, most preferably isopropanol. In a preferred embodiment, the method is carried out in isopropanol and 6M hydrochloric acid. The reaction can be carried out between −10° C. to 60° C., preferably between 0° C. and 25° C.

The method provides a highly purified crystallized preparation of swainsonine salts preferably hydrochloride swainsonine salts.

Step (A)

A method of the invention may comprise reacting a lactone of the formula II with diisobutylalumnium hydride in an organic solvent to obtain a lactol of the formula III. The organic solvent is preferably selected from the group consisting of toluene, benzene, xylene, chlorobenzene, and t-butyl methyl ether. Preferably the reaction is carried out using toluene which is easy to dry and is less volatile than conventional solvents such as THF. The reaction is carried out between −40° C. and 0° C., most preferably between about −20° C. to −40° C.

In order to avoid the formation of an undesirable gel reaction product, a small amount of brine (i.e. NaCl concentrate in a concentration of <1/2%) or concentrated NaOH is added to the reaction mixture. In particular, NaCl is stirred with the crude reaction products until a precipitate forms; a desicating agent (e.g. $Na_2SO_4$) is added to the mixture of water/toluene/THF reaction products and stirred for extended periods of time. The resulting hydrated $Na_2SO_4$ is easily filtered and the filtrate does not contain aluminum byproducts. The product is isolated as a clear solution. This work-up differs from conventional methods, which use $MgSO_4$ which forms a gel of magnesium and aluminum salts.

In an embodiment of the invention Step (A) comprises (i) reacting 2,3-O-alkylidene-D-erythrolactone, e.g., 2,3-O-isopropylidene-D-erythrolactone ((−)-(3aR-cis)-dihydro-2,2-dimethylfuro[3,4-d]-1,3-dioxol-4(3aH)-one), with a molar equivalent of diisobutylalumnium hydride in toluene, at about −10° C. to 0° C. (preferably 0° C. in an embodiment of the invention); (ii)(a) adding methanol; (ii)(b) adding THF and brine, (ii)(c) adding disodium sulfate, and (ii)(d) removing inorganic salts by precipitation and filtration to yield 2,3-O-alkylidene-D-erythrose (the lactol).

The lactone of the formula II may be prepared from D-isoascorbic acid using a novel method (see for example Steps 1 and 2, Scheme IV). In particular, 2,3-O-isopropylidene-D-erythronolactone may be prepared from potassium erythronate and ketone or orthoester with a catalytic acid. The method comprises (a) reacting D-isoascorbic acid with a base (e.g., aqueous sodium carbonate) and hydrogen peroxide; and (b) neutralizing excess base with a protonic acid (e.g. HCl) to a pH between 3.5 and 4.5, preferably 3.5 and 4.2, more preferably between 3.8 and 4.0, and most preferably 4.0; (c) replacing the water with a miscible organic solvent and filtering the precipitated inorganic salts; (d) adding a catalytic sulfonic acid in a ketone or an orthoester, and magnesium sulfate; and (e) crystallizing 2,3-O-isopropylidene erythronolactone preferably from ether/hexanes, or combinations of t-butyl methyl ether and diisopropyl ether with hexanes or petroleum ether.

Examples of catalytic sulfonic acids include catalytic amounts of p-toluene sulfonic acid, methane sulfonic acid, sulfuric acid, camphor sulfonic acid, sulfonic acid resins, acidic zeolites or clays. The ketone may be acetone, methyl ethyl ketone, or cyclohexanone, preferably acetone. Examples of orthoesters include trimethyl orthoethyl, orthoformate, orthoacetate, orthobenzoate, or orthopropionate. A solvent may be selected so that it is the same solvent used in the previous or subsequent steps in a method of the invention. Generally, it is important to evaporate the solvent as far as possible to precipitate unwanted salt. Therefore, in order to isolate product in high yield it is desirable to continuously or in a stepwise manner precipitate the salts and simultaneously evaporate the water. Using this procedure, a substantially salt free solution may be obtained.

The method for preparing the lactone is particularly useful for large scale processes (e.g. about 1 Kg scale) and provides a high yield of lactol compound (e.g. about 77%) compared to prior art methods.

Step (B)

A method of the invention may comprise reacting the lactol compound of the formula III with a phosphonium bromide salt (e.g. ethyl 4-triphenylphosphonium butyrate bromide salt) to obtain an olefinic alcohol of the formula IV. The phosphonium bromide salt may be prepared using a novel method (see for example Scheme IV) which comprises reacting ethyl 4-bromobutyrate with triphenyl phosphine in a high boiling solvent (e.g. n-butyl acetate or methyl ethyl ketone) at high temperatures (e.g. 130° C.) to form the phosphonium bromide salt. Using this method substantially all the phosphonium bromide salt precipitates from solution in high yield (<90%).

The reaction step preferably uses potassium tert-butoxide as a base instead of compounds such as LDA, lithium hexamethyldisilylamide (HMDS), sodium HMDS, and potassium HMDS which are used in conventional methods and are more expensive or difficult to work with. Therefore, the reaction may be carried out at temperatures between −15° C. to −20° C. The product is preferably isolated by adding ethanol and heating at reflux to regenerate the desired ethyl ester product from transesterified byproducts. Refluxing with any other desired alcohol will produce the corresponding ester product. The reaction provides a yield of about 70–75% which is significantly higher than reported methods.

Step (C)

The olefinic alcohol of the formula IV may be converted to the azide of the formula V using a Mitsunobu reaction. In particular, a method of the invention may comprise reacting an olefinic alcohol of the formula IV with a phosphine, dialkylazodicarboxylate, and azide source to obtain an azide of the formula V. The azide product is made as a stable species at low ambient temperatures. Examples of phosphines which may be used include trialkyl phosphines such as trimethylphosphine, and triaryl phosphines, such as triphenylphosphine, tribenzyl phosphine, and paramethylphenyl phosphine. Examples of dialkylazodicarboxylates that may be used in the process include diethylazodicarboxylate. (DEAD), dimethylazodicarboxylate, dibutylazodicarboxylate, or diisopropylazodicarboxylate (DIAD). Azide sources include azido trimethylsilane (TMS-$N_3$), diphenylphosphorylazide, tetrabutylammonium azide, and hydrazoic acid. The reaction may use a Crown ether and a metal azide including potassium azide, lithium azide, or sodium azide. The reaction typically uses tetrabutyl ammonium fluoride (TBAF) to remove any reaction byproducts if TMS-$N_3$ is used. The reaction is generally carried out at low temperatures, for example 10 to −25° C.

An embodiment of Step (C) comprises (i) reacting the olefinic alcohol of the formula IV with a molar equivalent of triphenyl phosphine in THF, a molar equivalent of diisopropylazodicarboxylate, and trimethylsilyl azide to form an alkyl azide product, e.g., (+)-(4R, cis)(Z)-2,2-dimethyl-5-(4-carbethoxy-1-butenyl)-1,3-dioxolane-4-azidomethane, and a byproduct, e.g., an O-trimethylsilyl-protected olefinic alcohol; (ii) adding tetrabutylammonium fluoride in THF to the crude azide product; (iii) repeating the treatments described in (i) and (ii), thereby converting a portion of the O-trimethylsilyl-protected olefinic alcohol byproduct into the alkyl azide product.

Step (C) produces the novel compound of the formula V

V

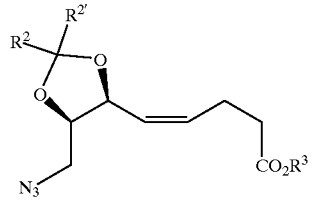

wherein $R^2$, $R^{2'}$ and $R^3$ are as defined above. In an embodiment $R^2$ and $R^{2'}$ are the same and represent $C_{1-4}$ alkyl. In a preferred embodiment, the compound of the formula V is ethyl (Z-5-[(4R,5S)-5-(azidomethyl-2,2-dimethyl-1,3-dioxolan-4-yl]-4-pentenoate.

Step (D)

A method of the invention may comprise refluxing the azide of the formula V in a non-reactive high boiling (e.g. >90° C.) solvent to form an imino ester of the formula VI. The solvent may be selected from the group consisting of toluene, benzene, xylene, chlorobenzene, and dimethyl formamide. Preferably the solvent is the same solvent used in prior and subsequent steps in a method of the invention, and most preferably is toluene.

An embodiment of Step (D) comprises refluxing the purified azide in toluene at an initial concentration of between 0.30 M and 0.05 M, preferably between 0.1M and 0.2M, to form an imino ester, e.g., (−)-(1S,5R)-3,3-dimethyl-8-(3-carbethoxy-1-propyl)-7-aza-2,4-dioxabicyclo[3.3.0]oct-7-ene.

Step (E)

A method of the invention may comprise reacting an imino ester of the formula VI with an alkali metal hydroxide in a mixture of water and a miscible non-reactive organic solvent and acidifying the reaction mixture to obtain an imino acid of the formula VII. Examples of miscible non-reactive organic solvents include $C_{1-4}$ alkanols as described herein and THF. Alkali metal hydroxides that may be used in the reaction include NaOH, LiOH, and KOH.

An embodiment of Step (E) comprises (i) reacting an imino ester of the formula VI with a molar equivalent of an alkali metal hydroxide in a mixture of water and a $C_{1-4}$ alkanol (e.g., ethanol); (ii) acidifying the reaction mixture to about pH 3–7, preferably 6–7, to yield an imino acid, e.g.,(−)-(1S,5R)-3,3-dimethyl-8-(3-carboxy-1-propyl)-7-aza-2,4-dioxabicyclo[3.3.0]oct-7-ene.

Step (F)

A method of the invention may comprise cyclizing an imino acid of the formula VII by refluxing in an organic solvent with a catalyst to form an enamide of the formula VIII while removing the water formed during the reaction. Organic solvents may be selected from the group consisting of toluene, benzene, xylene, chlorobenzene, and t-butyl methyl ether. Preferably, the solvent is a solvent used in prior or subsequent steps in a method of the invention. The enamide is isolated and dissolved in an anhydrous environment using the selected solvent, preferably toluene. The catalyst may be a Lewis acid in particular a carboxylic acid or sulfonic acid including but not limited to formic acid, acetic acid, trifluoroacetic acid, propionic acid, butyric acid, trichloroacetic acid, toluene sulfonic acid, camphor sulfonic acid, sulfuric acid, methane sulfonic acid, benzoic acid, or HCl gas. Preferably the catalyst is a lower alkyl carboxylic acid such as formic acid, acetic acid, trifluoroacetic acid, propionic acid, butyric acid, or trichloroacetic acid.

The enamide may be used as a starting material to prepare various derivatives of swainsonine including derivatives of swainsonine substituted at the 5, 6, 7, or 8 positions, or combinations thereof.

In an embodiment of the invention Step (F) comprises cyclizing an imino acid of the formula VII by refluxing in toluene with a catalytic amount of a lower alkyl carboxylic acid to form an enamide, e.g., (−)-(7S,8R)-7,8-O-isopropylidenedioxy-2-oxo-1-azabicyclo [4.3.0]non-5-ene.

Step (G)

A method of the invention may comprise reducing an enamide of the formula VIII with a borane reagent in an organic solvent and oxidation (e.g. peroxide oxidation) of the resulting alkyl borane to obtain a protected swainsonine of the formula I. For the reduction, the organic solvent may be selected from the group consisting of toluene, THF, benzene, xylene, chlorobenzene, blends of petroleum ether, ether, t-butyl methyl ether ethylformate, ethyl acetate/hexane, ethyl acetate/petroleum ether, or ethyl acetate/heptane. Preferably the solvent is the same solvent used in prior and subsequent steps in a method of the invention and is most preferably toluene. The borane reagent which may be used may be borane-THF complex, borane dimethyl sulfide complex, or a mono- or disubstituted borane such as methyl- or dimethyl thexyl, 9-BBN, or monochloroborane.

An embodiment of Step (G) of the invention comprises (i) reducing the enamide with borane-THF in toluene; (ii) crystallizing the alkylidenedioxy-8-hydroxyindolizidine, e.g., swainsonine acetonide, from t-butyl methyl ether, ethyl acetate, ethyl acetate/hexane, ethyl acetate/petroleum ether, or ethyl acetate/heptane.

DETAILED DESCRIPTION OF PREFERRED EMBODIMENTS

Swainsonine Halide Salts

A preferred method of the invention for preparing a halide salt of swainsonine includes the following steps (A) through (H) as follows.

(A)(i) reacting a 2,3-O-alkylidene-D-erythrolactone, e.g., 2,3-O-isopropylidene-D- erythrolactone ((−)-(3aR-cis)-dihydro-2,2-dimethylfuro[3,4-d]-1,3-dioxol-4(3aH)-one), with a molar equivalent of diisobutylaluminium hydride in tetrahydrofuran, or preferably toluene, at about −10° C. to 0° C. (in an embodiment 0° C.);

(A)(ii)(a) adding methanol, (ii)(b) concentrating to a gel, (ii)(c) adding THF and brine, (ii)(d) adding disodium sulfate, and (ii)(e) removing inorganic salts by precipitation and filtration to yield 2,3-O-alkylidene-D-erythrose (the lactol);

(B)(i) reacting ethyl 4-bromobutyrate with triphenyl phosphate to form a phosphonium bromide salt;

(B)(ii) reacting the ylide generated from the phosphonium salt with the 2,3-O-alkylidene-D-erythrose to form an olefinic alcohol;

(C)(i) reacting the olefinic alcohol with a molar equivalent of triphenyl phosphine in THF, a molar equivalent of diisopropylazodicarboxylate, and trimethylsilyl azide to form an alkyl azide product, e.g., (+)-(4R, cis)(Z)-2,2-dimethyl-5-(4-carbethoxy-1-butenyl)-1,3-dioxolane-4-azidomethane, and a byproduct, e.g., an O-trimethylsilyl-protected olefinic alcohol;

(C)(ii) adding tetrabutylammonium fluoride in THF to the crude azide product;

(C)(iii) repeating the treatments described in (C)(i) and (C)(ii), thereby converting a portion of O-trimethylsilyl-protected olefinic alcohol byproduct into the alkyl azide product (D) refluxing purified azide in toluene at an initial concentration of between 0.30 M and 0.05 M to form an imino ester, e.g., (−)-(1S,5R)-3,3dimethyl-8-(3-carbethoxy-1-propyl)-7-aza-2,4-dioxabicyclo [3.3.0] oct-7-ene;

(E)(i) reacting the imino ester with a molar equivalent of an alkali metal hydroxide in a mixture of water and a $C_{1-3}$ alkanol (e.g., ethanol);

(E)(ii) acidifying the reaction mixture to about pH 3–7, preferably 6–7, to yield an imino acid, e.g.,(−)-(1S,5R)-3,3-dimethyl-8-(3-carboxy-1-propyl)-7-aza-2,4-dioxabicyclo[3.3.0]oct-7-ene;

(F) cyclizing the imino acid by refluxing in toluene with a catalytic amount of a lower alkyl carboxylic acid to form an enamide, e.g., (−)-(7S,8R)-7,8-O-isopropylidenedioxy-2-oxo-1-azabicyclo[4.3.0]non-5-ene;

(G)(i) reducing the enamide with borane-THF complex in toluene followed by peroxide oxidation;

(G)(ii) crystallizing the alkylidenedioxy-8-hydroxyindolizidine, e.g., swainsonine acetonide, from t-butyl methyl ether, ethylformate, ethyl acetate/hexane, ethyl acetate/petroleum ether, or ethyl acetate/heptane;

(H)(i) converting alkylidendioxy-8-hydroxyindolizidine to the swainsonine salt by acid hydrolysis in the presence of a $C_{1-3}$ alkanol (e.g., isopropanol) at room temperature; and optionally (H)(ii) recrystallizing the swainsonine salt in a $C_{1-3}$ alkanol (e.g., isopropanol).

In particular embodiments, methods are provided for synthesizing swainsonine salts comprising Step (H); Steps (F) and (H); Steps (G) and (H); Steps (E) and (H); Steps (C) and (H); Steps (C), (D), and (H); Steps (A)(i) and (H); Steps (A) and (H); Steps (B) and (H); Steps (C), (D), (E), (F), (G), and (H); Steps (A), (B), (D), and (H); Steps (A), (B), (C), (D), and (H); or Steps (C), (E), (F), and (H).

A particular synthesis of swainsonine halide salts, e.g., swainsonine hydrobromide or swainsonine hydrochloride is described in Schemes I–III. Scheme I converts D-isoascorbic acid to 2,3-O-isopropylidene-D-erythronolactol through the D-erythronolactone. Scheme II takes the lactol to the olefinic azide, and Scheme III converts the olefinic aside to swainsonine hydrochloride. Another specific route of synthesis contemplated by the present invention is shown in Scheme IV.

While it is easily recognized that the safer, most cost-efficient and energy-efficient synthesis utilizes all of the disclosed steps, individual steps may be inserted into known syntheses, such as the Cha synthesis (Supra), to provide the advantages of the selected step or steps. It will also be appreciated that protecting groups other than alkylidene (e.g isopropylidene) groups may be used in the detailed methods described herein.

The synthetic details follow Schemes I–V and Table A.

SCHEME I

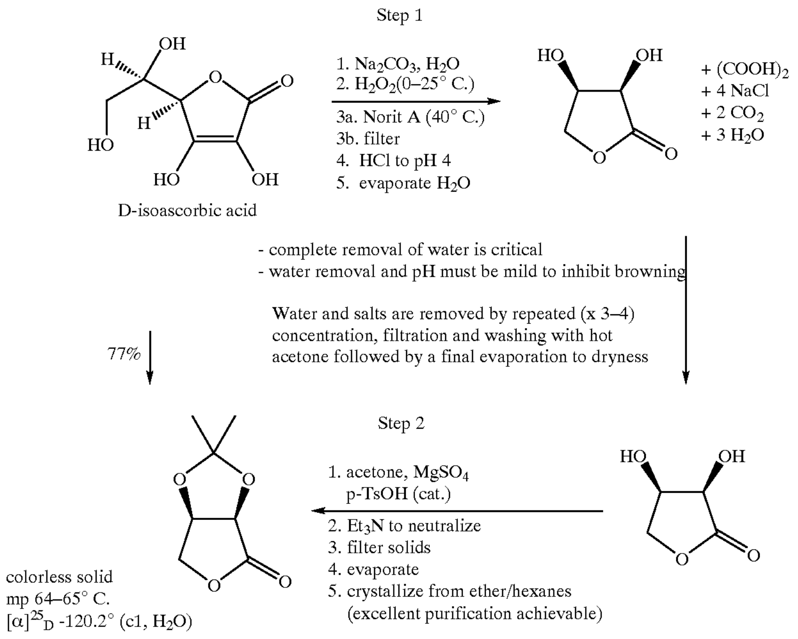

-continued
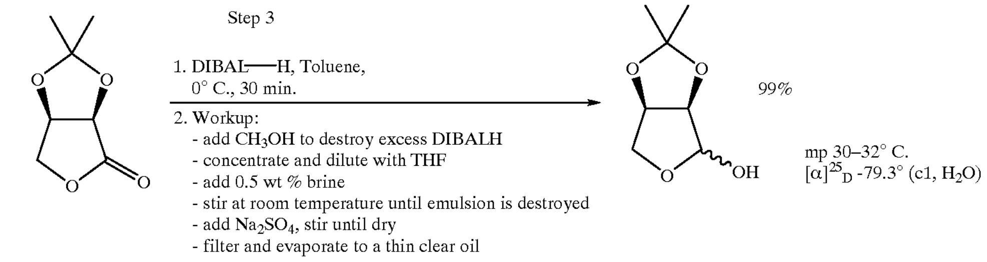
SCHEME II
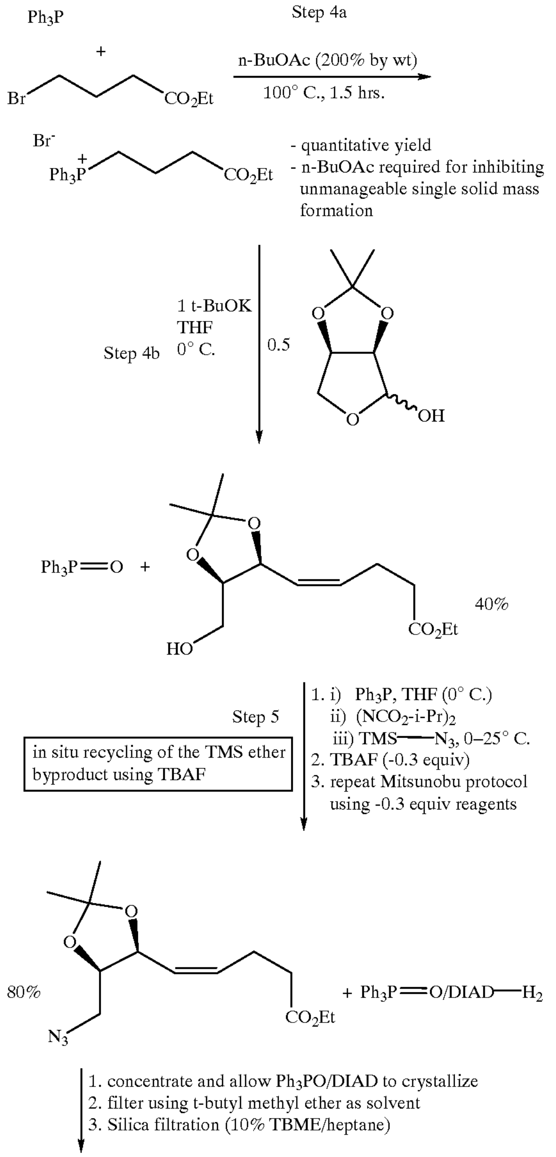
SCHEME III
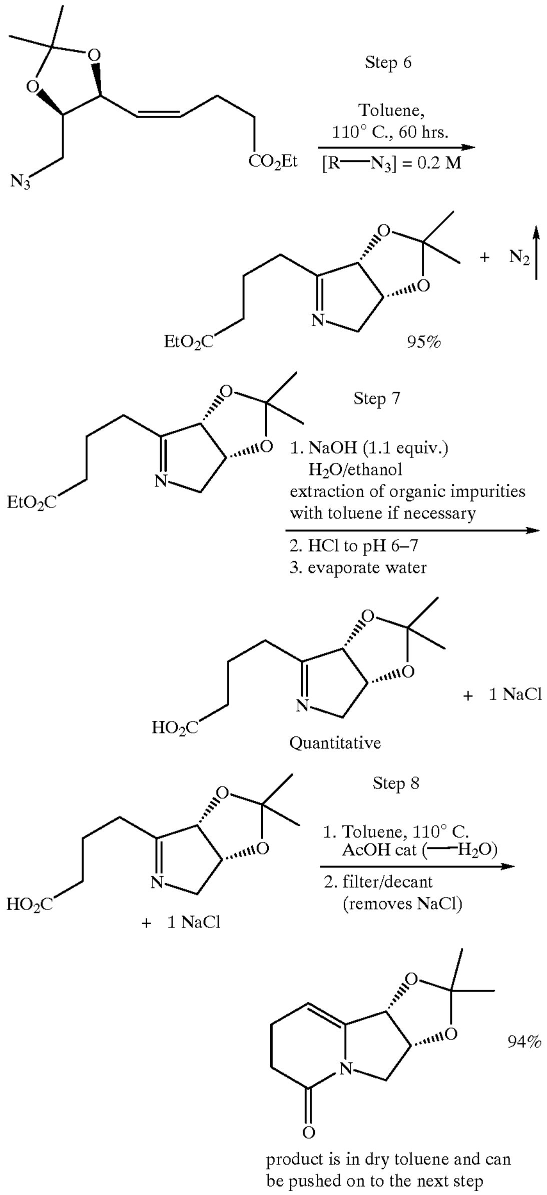

-continued
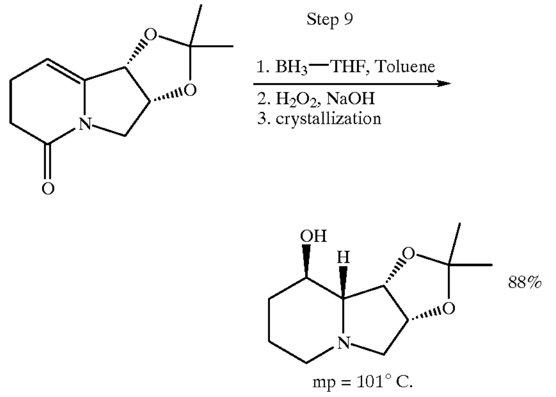
-continued
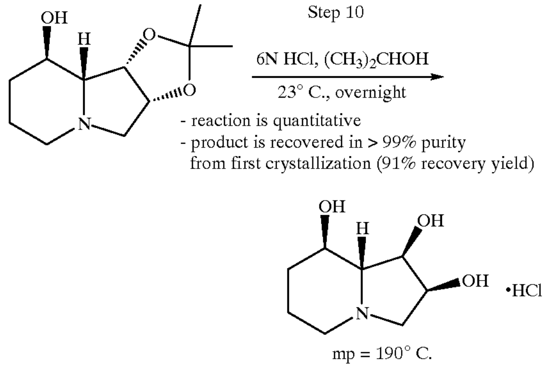
SCHEME IV
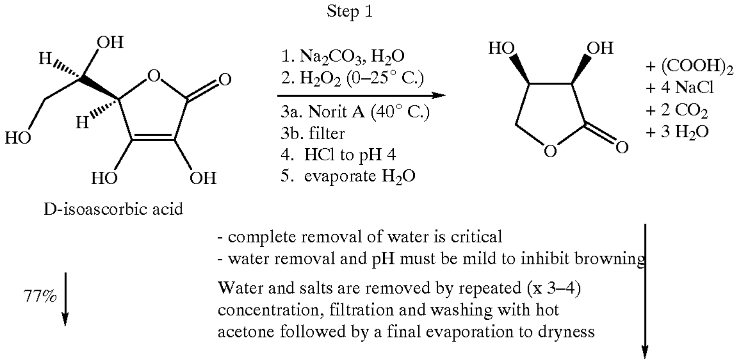
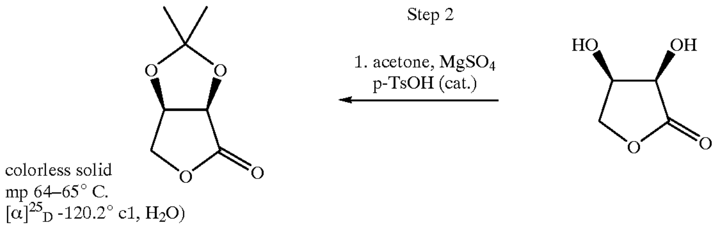
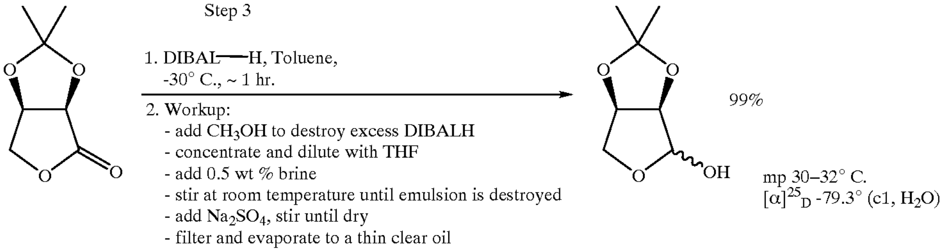

-continued
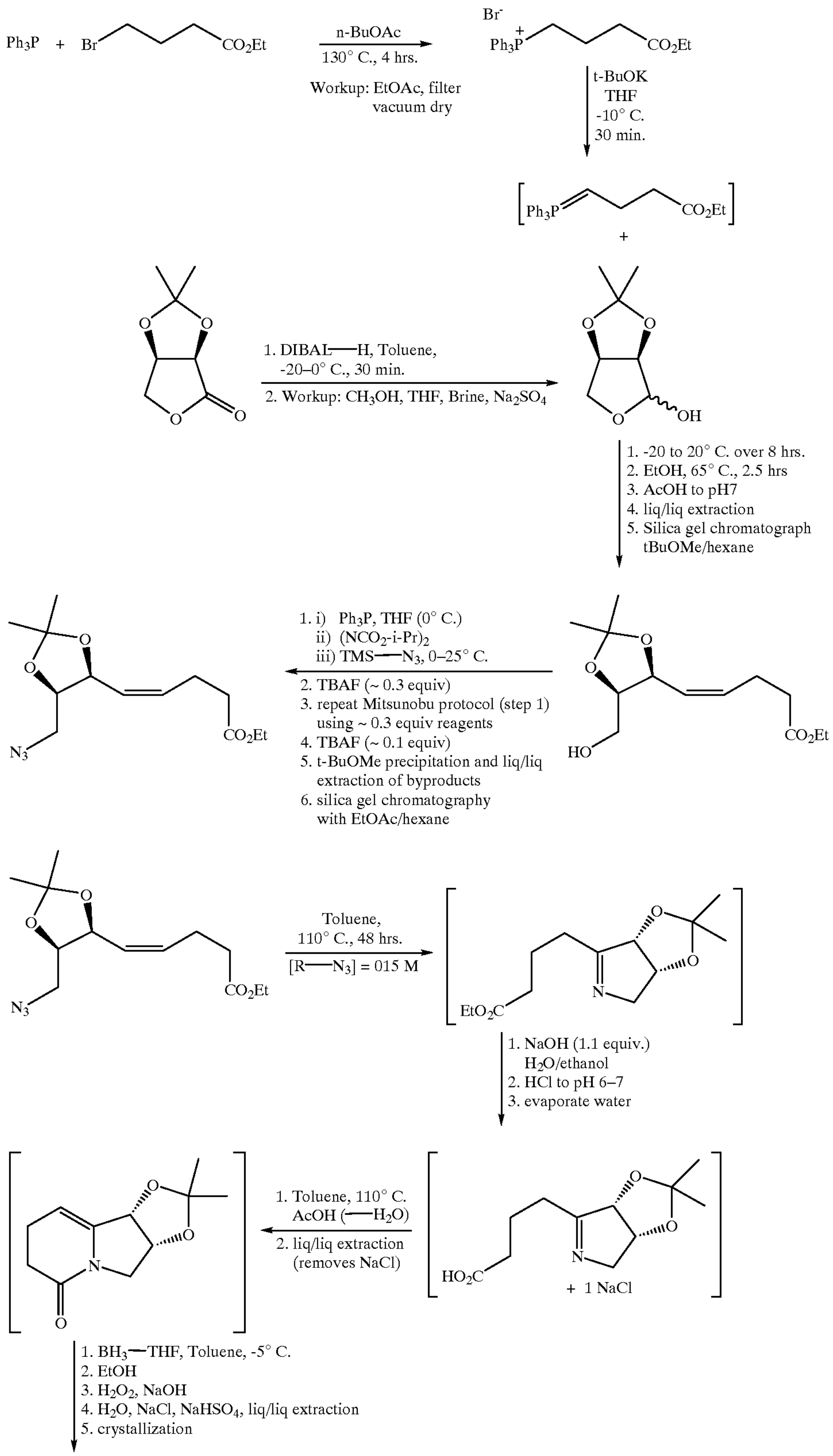

-continued

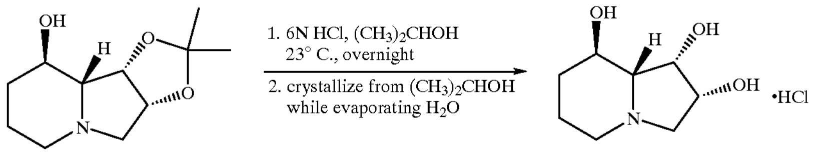

TABLE A ethyl 4-bromo butyrate
ethyl 4-bromobutanoate

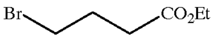

Molecular formula = $C_6H_{11}BrO_2$
Molecular Weight = 195.054
bp = 80–82° C./10 mm Hg 2,3-O-isopropylidene-D-erythronolactone

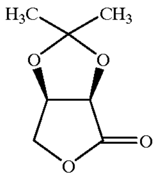

Molecular formula = $C_7H_{10}O_4$
Molecular Weight = 158.152
mp = 64–65° C.
$[\alpha]_D$ = −120.2° (c 1, $H_2O$)

(9Cl) CA Index Name:
Furo[3,4-d]-1,2-dioxol-4(3aH)-one, dihydro-2,2-dimethyl-,(3aR, 6aR)-
Registry 25581-41-3

2,3-O-isopropylidene-D-erythronolactol

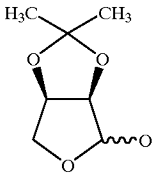

Molecular formula = $C_7H_{12}O_4$
Molecular Weight = 160.168
mp = 30–32° C.
$[\alpha]_D$ = −79.3° (c 1, $H_2O$)

(9Cl) CA Index Name:
1,3-Dioxolane-4-carboxaldehyde, 5-(hydroxymethyl)-2,2-dimethyl-,(4R-cis)-
Registry 51607-16-0 phosphonium bromide salt

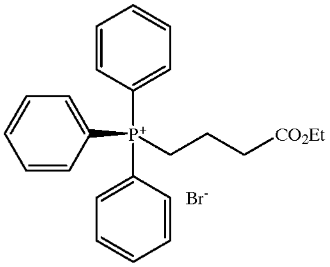

Molecular formula = $C_{24}H_{25}O_2PBr$
Molecular Weight = 457.340
Mp = 159–160° C. (n-BuOAc)

(9Cl) CA Index Name:
Phosphonium, (4-ethoxy-4-oxobutyl)triphenyl-, bromide
Registry 50479-11-3

Olefinic alcohol

TABLE A-continued

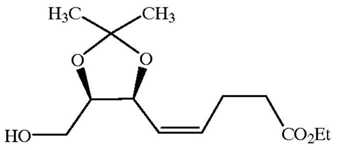

Molecular formula = $C_{13}H_{22}O_5$
Molecular Weight = 258.311
pale oil
$[\alpha]_D = -29.3°$ (c 3.3, $CHCl_3$)

(9Cl) CA Index Name:
4-Pentenoic acid, 5-[5-(hydroxymethyl)-2,2-dimethyl-1,3-dioxolan-4-yl]-, ethyl ester, [4S-[4.alpha. (Z), 5.alpha.]]-
Registry 119011-34-6

Olefinic azide

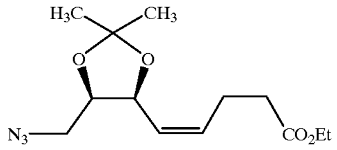

Molecular formula = $C_{13}H_{21}N_3O_4$
Molecular Weight = 283.324
(+)-(4R,cis)(Z)-2,2-dimethyl-5-(4-carbethoxy-1-butenyl)-1,3-dioxolane-4-methanol
ethyl(Z)-5-[(4R,5S)-5-(azidomethyl-2,2-dimethyl-1,3-dioxolan-4-yl]-4-pentenoate Imino ester

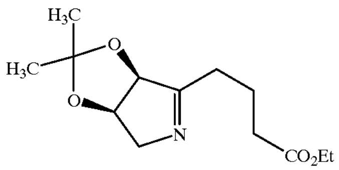

Molecular formula = $C_{13}H_{21}NO_4$
Molecular Weight = 255.310

(9Cl) CA Index Name:
4H-1,3-Dioxolo[4,5-c]pyrrole-6-butanoic acid, 3a, 6a-dihydro-2,2-dimethyl-, ethyl ester, (3aR-cis)-
Registry 119011-33-5

Imino acid

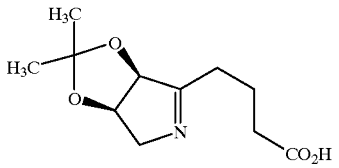

Molecular formula = $C_{11}H_{17}NO_4$
Molecular Weight = 227.257

(9Cl) CA Index Name:
4H-1,3-Dioxolo[4,5-c]pyrrole-6-butanoic acid, 3a, 6a-dihydro-2,2-dimethyl-, (3aR-cis)-
Registry 119011-36-8

Enamide

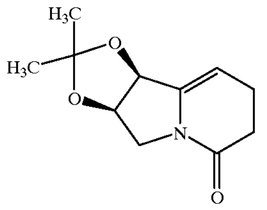

Molecular formula = $C_{11}H_{15}NO_3$
Molecular Weight = 209.242

(9Cl) CA Index Name:
1,3-Dioxolo[4,5-a]indolizin-6(4H)-one, 3a, 7, 8, 9b-tetrahydro-2,2-dimethyl-, (3aR-cis)-
Registry 130412-70-3

Swainsonine acetonide

TABLE A-continued

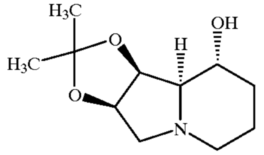

Molecular formula = $C_{11}H_{19}NO_3$
Molecular Weight = 213.274
mp = 101–103° C. (EtOAc)
$[\alpha]_D$ = −72.8° (c 0.4, MeOH)

(9Cl) CA Index Name:
1,3-Dioxolo[4,5-a]indolizin-9-ol, octahydro-2,2-dimethyl-, [3aR-(3a.alpha., 9.alpha., 9a.alpha., 9b.alpha.)]-
Registry 85624-09-5

Swainsonine

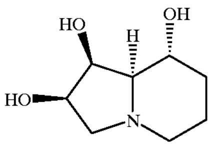

Molecular formula = $C_{11}H_{19}NO_3$
Molecular Weight = 213.274

(9Cl) CA Index Name:
1,2,8-indolizinetriol, octahydro-, [1S-(1.alpha., 2.alpha., 8.beta., 8a.beta.)]-
Registry 72741-87-8

Swainsonine hydrochloride

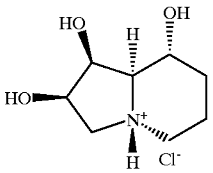

Molecular formula = $C_8H_{16}NO_3Cl$
Molecular Weight = 209.671
Mp = 189–191° C.
$[\alpha]_D$ = −66° (c 1, $H_2O$)

Name:
1,2,8-indolizinium, octahydro-, [1S-(1.alpha., 2.alpha., 8.beta., 8a.beta.)]-, chloride The following non-limiting examples are illustrative of the present invention:

EXAMPLE 1

D-Erythronolactone from D-Isoascorbic acid

With the modifications discussed below, the procedure of H. Cohen et. al. (J. Am. Chem. Soc. (1983), 105:3661–3672/ Org. Synth. (1985), 63:127–135) was followed using 176.0 g (1.0 mole) D-isoascorbic acid, 2.5 liters deionized water, 212 g (2.0 mole) $Na_2CO_3$, 220 mL (2.7 mole) 30% $H_2O_2$, and 42 g Norit A charcoal. Notably, the pH was adjusted to 3.5, in contrast to the Cohen procedure which required a pH adjustment to ~1 with HCl to gas off all the carbonate used. The Cohen procedure resulted in a very acidic crude product that browned quickly as water was evaporated. According to the present invention, a pH of 3.5 was sufficient for gassing off the carbonate and resulted in a crude product that was less acidic, and therefore less susceptible to browning. Preferably, the pH is adjusted to between 3.9–4.0, as indicated by the cessation of carbon dioxide evolution. Alternatively, neutralization with NaOH may also be considered before water removal.

The water was removed under vacuum until a thick slurry of product and insoluble salts was obtained. The mixture was filtered and the residue washed with hot acetone. The filtrate was again concentrated until additional insoluble material could be filtered and the residue was rinsed with hot acetone. This process was repeated until no salts could be precipitated. In general, three or four cycles were sufficient to remove the water and salts. The resulting solution was dried under vacuum and the residue pushed on to the next step. The physical properties of the product match those reported in the literature.

EXAMPLE 2

Isopropylidenation of D-Erythronolactone

To the crude material from Example 1 dissolved in acetone (1000 mL) was added 100 g of $MgSO_4$ followed by 2.1 g p-toluenesulfonic acid monohydrate. After stirring the solution at room temperature for 24 hours, complete consumption of the diol ($R_f$=0) to the desired acetonide ($R_f$=0.6) was shown by TLC (1:1::ethyl acetate:toluene). The pH was slowly adjusted to pH 7 using triethyl amine, while keeping the temperature at 0° C. Filtration followed by solvent evaporation under vacuum gave a brown oil. Crystallization was achieved at room temperature by adding hexane to a solution of the crude product mixture in diethyl ether. In other trials, the product was crystallized successfully from t-butyl methyl ether(TBME)/hexane or TBME/heptane, which are less flammable than diethyl ether. Filtration, washing with 1:2::ether:hexane, and drying under vacuum yielded 149.1 g of white crystalline (77.4%, 2 steps from D-isoascorbic acid). Very little additional product was detected in the mother liquor.

According to the present method, omitting 2,2-dimethoxy propane resulted in no detectable acyclic methyl ester byproduct or other byproducts described by L. A. Flippin and C. H. Heathcock, Org. Synth. (1985) 63:127–135. In a reference trial following the Cohen procedure, which includes dimethoxy propane/acetone, the corresponding acyclic methyl ester side product was formed in ~10% yield presumably due to the large amount of methanol generated from the 2,2-dimethoxy propane.

Combined modifications in Examples 1 and 2 have increased the yield and the product quality to achieve crystallization at room temperature for a cleaner material. It is recognized that other alkylidene protecting groups may easily be substituted for isopropylidene. The physical properties of the product match those reported in the literature.

EXAMPLE 3

2,3-O-Isopropylidene-D-erythronolactol

Reference Examples 3a and 3b are provided to demonstrate the advantages of Examples 3c and 3d, the latter two describing methods of the invention which have lower energy requirements and lower costs. The reaction was essentially quantitative when performed at 0° C. in anhydrous toluene (Example 3c). While THF produced a greater exotherm and lower yield (90%) than toluene, both work up and solvent removal were easier with THF (Example 3d). It is important to remove as much toluene as possible immediately after the reduction and methanol quench for large scales (<1 kg). Otherwise, the formation of a thick gel of complexed aluminum salts requires addition of one volume of THF followed by brine. Additional stirring is also necessary after addition of disodium sulfate to maintain product recovery. Without stirring, the desired product may be absorbed or chelated in aluminum salt complexes within the filter cake.

EXAMPLE 3a 2,3-O-isopropylidene-D-erythronolactone (59 g; 373 mmole) was dissolved in 800 mL of dry toluene (distilled from sodium/benzophenone) and the solution cooled to −60° C. Diisobutylaluminum hydride (DIBALH; 476 mL; 1M solution in toluene) was slowly added over 1 hour while maintaining the low temperature. The mixture was stirred for an additional 1.5 hours at −60° C. after the completion of the DIBALH addition. The reaction was quenched by adding 50 mL of methanol and concentrated until the formation of a gel (~200 mL mixture volume). Tetrahydrofuran (400 mL) was added, followed by brine (25 mL). The solution became increasingly cloudy over approximately 20 minutes, until no more white solid appeared. After addition of powdered anhydrous sodium sulfate (100 g), the solution was stirred for 15 minutes and filtered through a glass fiber filter pad. The filtrate evaporated to give the lactol as a slightly yellow thin oil. The oil was dried under vacuum for two days to give 58.4 g (97.7% yield) of the lactol which crystallized upon standing at room temperature.

The reaction was followed by TLC using 1:1::toluene:EtOAc. The lactone was cleanly converted to the lactol with only a trace of baseline material. $R_f$=0.63 for the lactone, $R_f$=0.44 for the lactol product. Although the reaction was relatively clean by TLC, yield obtained according to the original method described by the Cohen procedure (J. Am. Chem. Soc., 1983) was not reproducible. Extractive workup was also not effective. The protocol described above was cleaner and faster. Similarly, the reaction and workup procedure by Pearson and Hembre (J. Org. Chem., 1996) was not as clean and was difficult to workup due to poor filtration properties of the crude product solution.

EXAMPLE 3b

THF

The Example 3a procedure was scaled to 1.0 g of 2,3-O-isopropylidene-D- erythronolactone and the reduction carried out at −30° C. The isolated yield was 98%.

EXAMPLE 3c

0° C., Toluene

The Example 3a procedure was scaled to 81.0 g of 2,3-O-isopropylidene-D- erythronolactone and the reduction carried out in toluene at 0° C. The reaction was completed in 25 minutes (the total time of DIBALH addition) and was clean by TLC. The isolated yield was 99%.

EXAMPLE 3d

0° C., THF

The Example 3a procedure was scaled to 1.0 g of 2,3-O-isopropylidene-D- erythronolactone and the reduction (1.2 equiv DIBALH) carried out at 0° C. in THF, resulting in a strong exotherm. The reaction was quenched with 1 mL methanol. After addition of 5 mL brine and stirring for 20 minutes, 10 g powdered $Na_2SO_4$ was added. After stirring for an additional 30 minutes, the solution was filtered through a 1 micron porosity glass fiber filter and the solvent evaporated. The isolated yield was 99%.

EXAMPLE 4

Ethyl butyrate 4-triphenyl phosphonium bromide salt

An excess of solvent (estimated 200%–300% of total reagent weight) should be used to ensure a free flowing product slurry for simple filtration and washing with ethyl acetate. There is an undetermined but manageable heat of crystallization associated with product formation.

EXAMPLE 4a

Moderate Scale

Ethyl 4-bromobutyrate ( 204.8 g; 1.05 mole) and triphenyl phosphine (275.0 g; 1.048 mole) were heated to 100° C. for 4 hours and cooled to room temperature. The resulting solid mass was crushed in ethyl acetate, filtered, and washed with ethyl acetate to give the desired salt in 431.5 g (90%) yield.

EXAMPLE 4b

Large scale

A 50 L flask was charged with 3.65 kg of triphenyl phosphine, 2000 mL of ethyl 4-bromo butyrate and 5 liters of n-butyl acetate. The heterogeneous solution was stirred at moderate speed while heating was started. The solution turned clear upon reaching 63° C. After slowly reaching 126° C. after 2 hours of heating, the reaction mixture was a very thick white slurry. Heating was continued for an additional one hour. Upon cooling to room temperature (e.g. 2 days), the slurry had hardened to a solid which was removed from the reaction flask by careful chipping with large spoons. The product was crushed and washed with ethyl acetate briefly on a large Buchner funnel. The final product was placed in trays and dried in a vacuum oven (70° C., 2 days) to remove any butyl acetate, yielding 6.15 kg white light solid (98%).

EXAMPLE 4c

Reference Examples (5 g Scales)

Adding 100% (vol/wt) n-butyl acetate gave, after 3 hours at 80–100° C., a near quantitative yield of filterable white crystalline solid. Substitution with methylethyl ketone gave a 90% yield after filtration. Refluxing in ethyl acetate overnight (50% and 100% (vol/wt)) only provided a 35% yield of the desired phosphonium salt after cooling and filtration. Yields ranged from 50% to 70% when benzene, toluene, xylene, or hexane was used as solvent.

EXAMPLE 5

Wittig Chain Extension to the Olefinic Alcohol

EXAMPLE 5a

A stirred suspension of the triphenyl phosphonium bromide salt (5.09 kg; 10.9 mole; 2 equiv) in anhydrous THF (8.5 L) was cooled to 10° C. Solid potassium t-butoxide (1.22 kg; 11.9 mole) was added slowly in small portions over a period of 20 minutes. Only a slight (~2° C.) exotherm was observed. The solution adopted a yellow to orange color as the potassium t-butoxide addition progressed. The solution was stirred for an additional 25 minutes while being cooled to −5° C., before the lactol was added. Pure lactol (940 g; 5.88 mole) was dissolved in 500 mL of dry THF and added in a dropwise fashion to the phosphonium salt mixture to avoid raising the temperature above 0° C. Addition of the lactol is exothermic, especially at the beginning of the addition. Upon completion of the the lactol addition, the reaction was allowed to reach room temperature overnight with stirring. The reaction appeared to be complete in 6 hours.

The reaction was cooled to 0° C. and slowly quenched with a 3.5 fold molar excess of 15% $NH_4Cl$ (8.2 L). A strong exotherm was observed with the addition of the first 100 mL of 15% $NH_4Cl$. The reaction was monitored by TLC (2:3::ethyl acetate:hexane, $R_f$=0.44 for lactol, $R_f$=0.38 for product) and appeared to give a very good conversion to the desired product. However, after quenching, work up, and chromatography multiple impurities appeared with the desired product.

The THF layer was separated from the aqueous layer. The aqueous layer was extracted with toluene (3.5 L, 3×2 L). Evaporation of solvent from the THF layer yielded an oil which was redissolved with the above toluene extracts. The combined solution was extracted with water (2×2500 mL) and brine (1×1000 mL). The organic extracts were dried over $MgSO_4$, filtered, and evaporated to yield a brown syrup containing solid triphenyl phosphine oxide. A filtration of only 10% by wt of expected triphenyl phosphine oxide was achieved after stirring the crude product syrup in t-butyl methyl ether at room temperature for 30 minutes. Evaporation of the TBME filtrate and organic washings gave a brown syrup (4 kg) which produced more $Ph_3PO$ upon standing at room temperature over the weekend. Repeated washing with TBME removed an additional 8% of the total expected $Ph_3PO$ only. Silica gel chromatography using TBME/hexane gave 695 g (45%) of desired product contaminated with modest amounts of side products. This material was pushed to the next synthetic step.

EXAMPLE 5b

Fitted with a mechanical stirrer, a dropping funnel and a nitrogen inlet, a 3-neck flask was charged with the phosphonium salt (339 g; 0.85 mole) from Example 4 and dry THF (800 mL). After cooling the solution to 0° C., potassium t-butoxide (95.4 g; 0.85 mole) was added in portions over a period of 30 minutes. The resulting yellow/orange solution was stirred for an additional 15 minutes before a solution of 2,3-O-isopropylidene-D-erythronolactol (68.0 g; 0.425 mole) in dry THF (400 mL) was added in a dropwise fashion. The internal temperature was maintained between 0–5° C. After 1 hour, TLC (2:3::ethyl acetate:hexane) showed a complete consumption of the lactol. Tetrahydrofuran was removed under vacuum. The residue taken up in toluene (2 L) and washed with water (3×750 mL) and brine (3×750 mL). The organic mixture was dried over $MgSO_4$, filtered and evaporated to a brown semisolid. The product was purified by silica gel chromatography using a gradient (0, 5, 10, 20, 30%) of t-butyl methyl ether and isolated as a yellow oil (46 g, 40%).

EXAMPLE 5c

Large Scale Protocol (Scheme V)

Scheme V

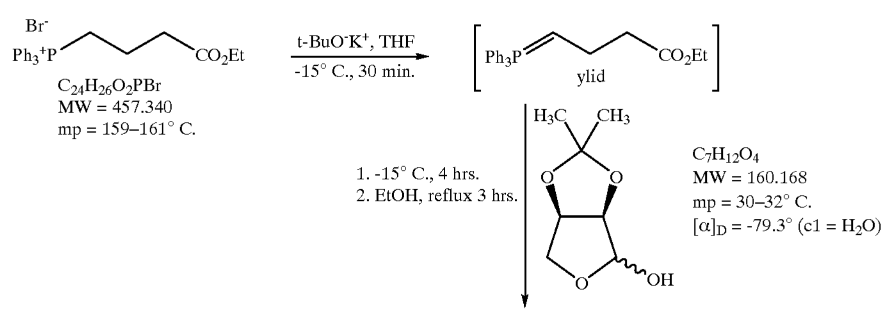

-continued

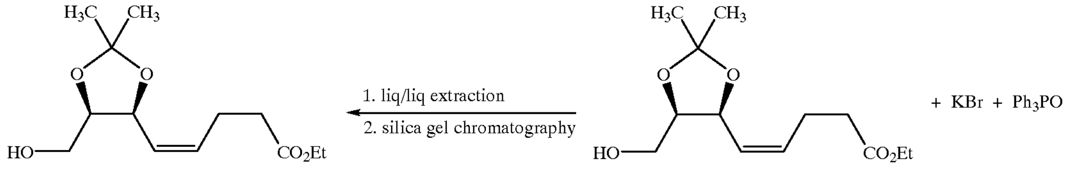

$C_{13}H_{22}O_5$
MW = 258.311
clear oil
$[\alpha]_D$ = -29.3° (c3.3, $CHCl_3$)

To a 72 L flask fitted with a mechanical stirrer, condenser, argon inlet, thermocouple, and heating/cooling bath was added ethyl 4-triphenylphosphonium butyrate bromide salt (12.8 kg, 28.0 mol) and anhydrous THF (34 L). After cooling the mixture to between −15 to −7° C. under argon, potassium tert-butoxide (3.67 kg, 32.7 mol) was added at a rate to maintain the reaction temperature less than −5° C. After 30 minutes, 2,3-O-isopropylidene-D-erythronoloactol (2.169 kg, 13.55 mol) dissolved in anhydrous THF (2.4 L) was added dropwise over 2 hrs. to the orange colored ylide solution such that the reaction temperature was maintained at less than −5° C. The reaction mixture was allowed to warm, with stirring, to ambient temperature (21° C.) overnight. To the resulting mixture was added anhydrous ethanol (6 L). The mixture was then heated to 65–69° C. for 2 hours whereupon the pH dropped from pH 14 to pH 11–12. The solution was cooled and glacial acetic acid (630 mL) was added (temperature: 0 to 5° C.) to adjust the pH to 7. The mixture was transferred to a 50 L distillation setup. The reaction flask was washed with 4 L toluene which was added to the distillation flask. The reaction mixture was concentrated under reduced pressure (pot temperatures from 8 to 20° C., approx. 10 torr, 20 to 30° C. bath). Then, 20 L toluene was added to the residue. Approximately half (11 L) of this mixture was transferred to a 35 L separatory funnel and washed with 3x5 L of water. During the second water wash, a denser third layer formed. This third layer was saved and the other water washes were discarded. The second half was then washed with 3x5 Liters of water and the third layer from the second wash was combined with the third layer from the first portion. The combined (3.5 L total) third dark oily layers were combined, diluted with 1.5 times its volume in ethyl acetate (5.25 L). The resulting mixture was washed with water (3.5 L). The ethyl acetate and toluene solutions were combined and concentrated under reduced pressure (15 to 30° C. at 10 torr) to afford 11.2 kg of a dark oil. The oil was mixed with 14.6 kg silica by weight. The 25.8 kg of adsorbed silica was divided into three equal portions (8.6 kg) and each were individually dry packed into a stainless steel MPLC unit on top of a 2.0 kg pad of fresh silica. The silica was compressed in the column with nitrogen at 25 psi for 20 minutes. Each portion was eluted with t-butyl methyl ether:hexane (2:8, 15 L, followed by 4:6, 45 L) at a rate of 400 mL/min (2 hours, 15–16 PSI). The combined eluents containing product (TLC) were concentrated to an oil under reduced pressure. The residue was further dried with stirring at less than 10 mm Hg for two hours and overnight without stirring. The resulting yellow oil was transferred to polyethylene containers product, 2.63 kg, 10.2 mol, (75%).

NMR results for the final product show greater than 92% purity with only triphenylphosphine oxide detectable as a contaminant.

EXAMPLE 6

Azide Preparation by a Mitsunobu Reaction

A reference example (Example 6a) is provided to demonstrate the advantages of the recycling reaction of the invention described in Example 6b.

EXAMPLE 6a

No Alcohol Recycling

Pure olefinic alcohol (214 g; 828 mmole) and triphenyl phosphine (248 g; 994 mmole; 1.2 equiv) were dissolved in dry THF (4 L). The solution was cooled to 0° C. and treated dropwise with 1.2 equivalents of DIAD (196 mL) while maintaining the temperature below 5° C. Continuing to maintain the temperature, dropwise treatment with 1.6 equivalents of TMS-azide (175 mL; 1.3 mole) formed a thick yellow precipitate. The final reaction solution was stored overnight at 4° C. and treated with tetrabutylammonium fluoride (TBAF) until the TMS ether side product was also converted to the alcohol. After concentration, the crude solid product was treated with TBME (600 mL). The insoluble triphenyl phosphine/dicarbisopropoxy hydrazine complex (304 g) was filtered and washed with additional TBME (2x150 mL). The TBME was evaporated to give an orange syrup (505 g) which was filtered in two batches through a short column of silica using a gradient of ethyl acetate/hexane to give 157 g (67%) of the desired azide after solvent removal. An earlier, similar trial on a 25 g scale had a 59% yield.

EXAMPLE 6b

Alcohol Recycling

To a cold (0° C.) and dry THF (500 mL) solution of the olefinic alcohol (30.0 g; 0.116 mole) and $Ph_3P$ (36.5 g; 0.139 mole) was slowly added DIAD (274 mL; 0.139 mole) under argon. Trimethylsilyl azide (185 mL; 0.139 mole) was added in a dropwise fashion, forming a yellow precipitate. After 20 minutes, TLC (3:7::ethyl acetate:hexane) showed complete consumption of the alcohol to give the desired azide and the TMS ether byproduct. Slow addition of 30 mL TBAF (1M in THF) resulted in conversion of the TMS ether back to the alcohol, as monitored by TLC. The concentrated residue was chromatographed on silica (10–20% TBME/hexane) to give pure azide and the recovered alcohol. Next, the alcohol was converted to more azide. Additional triphenyl phosphine (11 g; 0.042 mole), 1,2-dicarbethoxyhydrazine (DIAD) (83 mL; 0.042 mole) and TMS-azide (56 mL; 0.042 mole) were added. After stirring overnight at 0° C., additional TBAF (22 mL, 1 M in THF) was added. After 35 minutes, no TMS ether and only a small amount of starting alcohol was detectable by TLC. The solvent was evaporated and after standing overnight at room temperature the triphenyl phosphine oxide/dicarbisopropoxy hydrazine complex precipitate was filtered and washed with TBME to yield a light yellow oil which was chromatographed as above. Total yield of azide=27.8 g (80%). $^1H$ NMR (500 MHz): d($CDCl_3$): 1.22 (t, 3H, J=7.1 Hz) 1.40 (s, 3H), 1.58 (s, 3H), 2.42 (m,4H),3.22 (m,2H), 4.18 (q,2H, J=7.1 Hz), 4.28 (m,1H), 5.02 (t,1H, J=7.9Hz), 5.45 (t,1H, J=8.8 Hz), 5.64 (m, 1H). $^{13}C$ NMR (125 MHz): d($CDCl_3$): 14.2, 23.3, 25.3, 27.8, 33.7, 51.6, 60.5, 72.9, 109.1, 125.6, 133.1, 172.5. ESI-MS: 306.2 ($M+Na^+$), 301.4 ($M+NH_4^+$), 284.2 ($M+H^+$), 256.0, 226,0,208.0. FTIR ($cm^{-1}$, neat): 2985 (m), 2936 (m), 2101 (s, $N_3$), 1734 (s, C═O), 1372 (m), 1244, 1214, 1163, 1086.

EXAMPLE 6c (Scheme VI)

formed. The reaction sequence was repeated by first adding 801 g (3.05 mol; 0.37 equiv) of triphenyl phosphine and 670 g (3.15 mol, 0.385 equiv) of DIAD to the reaction mixture. After the mixture was stirred for 1 hour, 387 g (3.36 mol, 0.41 equiv) of TMS-azide was then added at a rate such that the pot temperature was maintained at 0–2° C. The reaction mixture was stirred for 1 hour. A total of 0.98 L of TBAF (1 M in THF) was then added to consume the TMS ether byproduct. The reaction mixture was allowed to warm to ambient temperature (20° C.) overnight with stirring. The Scheme VI

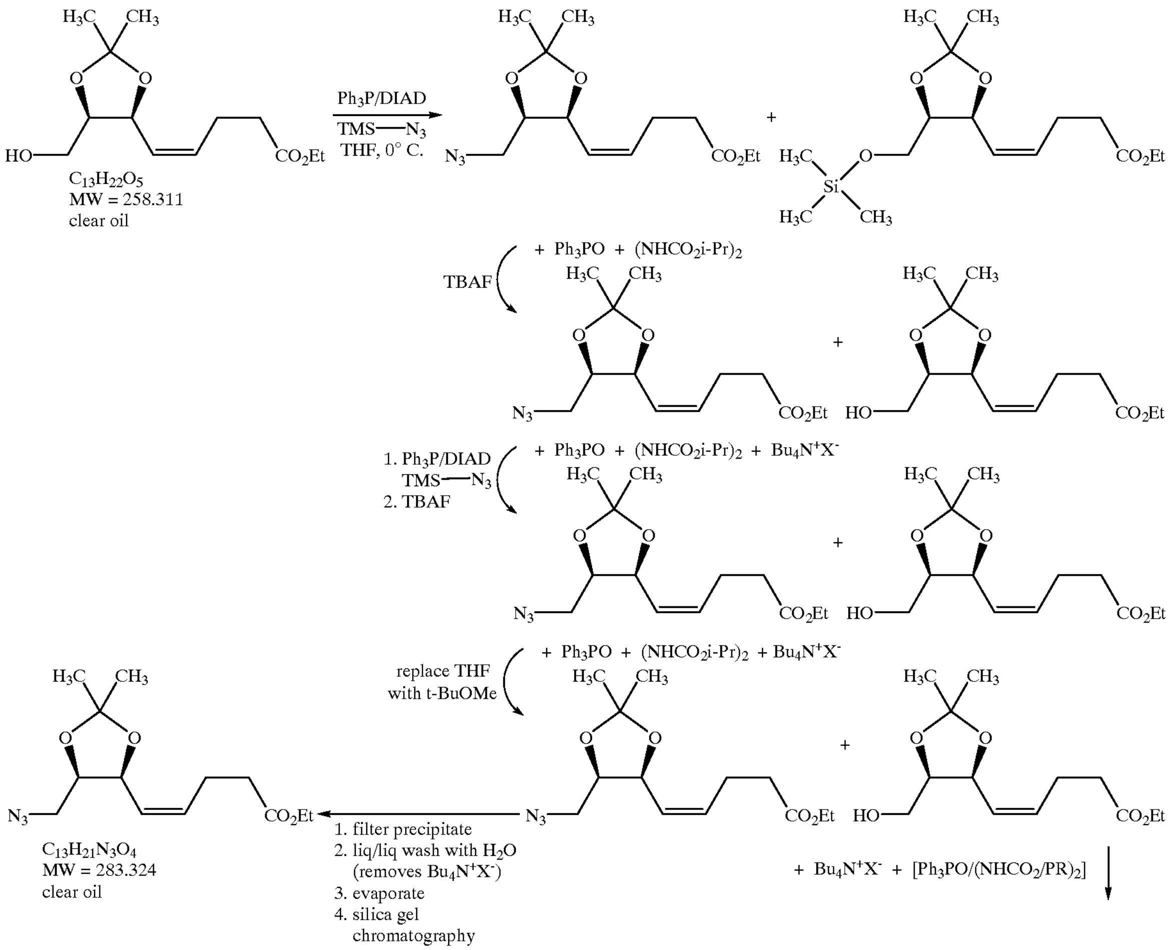

To a 72 L flask charged with an argon atmosphere, fitted with a mechanical stirrer and an addition funnel was added 2110 g (8.17 mol, 1 equiv) of olefinic alcohol, 34 L of anhydrous THF, and 2.36 kg (9.00 mol, 1.1 equiv) of triphenylphosphine. After the resulting mixture was cooled to −3° C., 1.90 kg (~9 mol, 1.1 equiv) of diisopropylazodicarboxylate (DIAD, Aldrich, 95%) was added at a rate to maintain the temperature ≦10° C. After stirring the mixture at 5–15° C. for 50 minutes, the reaction mixture was cooled to 0° C. To the cooled mixture was added 1.08 kg (~9 mol, 1.1 equiv) of trimethylsilyl azide over a 25 minute period while maintaining the pot temperature between 1 and 8° C. The resulting mixture was stirred for 1 hour at 5° C. until consumption of the alcohol was deemed complete by TLC. The reaction was cooled to 5° C. and a total of 2.2 L of tetra-n-butyl ammonium fluoride (TBAF, 1 M in THF) was added to completely consume the TMS ether byproduct THF was removed by vacuum distillation and the reaction vessel vented with argon. To the resulting residue, was added 10 L of a 80:20 mixture of MTBE:hexanes. The resulting slurry was stirred for 18 hours and filtered. The filter cake (a 1:1 complex of $Ph_3PO$:dicarbisopropoxy hydrazine complex ) was rinsed with 8 L of an 80:20 mixture of MTBE:hexanes. The filtrates were combined and washed twice with 4 L of water to remove tetrabutyl ammonium salts. The organic phase was concentrated by vacuum distillation to afford 3060 g of a viscous oil. The residue was mixed with 3.67 kg of silica gel (230–400 mesh) to afford a free-flowing material. The crude azide was purified by silica gel filtration/chromatography on a large MPLC column (same as for the olefinic alcohol) as follows: The adsorbed silica mixture was split into two unequal portions. The first portion of 4.59 kg was loaded onto a 14.5x93 cm length stainless steel column (capacity: 15.9 L) containing 5 kg of clean silica gel. Product was eluted with 24 L of 3% ethyl acetate: hexane mixture and 15 L of 5% ethyl acetate: hexane mixture by 20 psi nitrogen pressure. A second column was run using the remaining 2.14 kg of silica absorbed with crude azide 1.9 kg of clean silica gel. Fractions containing product were combined and concentrated by vacuum distillation to afford 1140 g of product. Yield=49%. (≧95% purity by $^1$H-NMR).

EXAMPLE 7

Azide to Swainsonine Acetonide

EXAMPLES 7a.

Cycloaddition to the Imino Ester

The azide (156 g; 0.524 mole) was refluxed in anhydrous toluene (3.5 L) for 95 hours. Solvent evaporation gave 143 g of crude product which was pushed on to the next step without further purification. Thin layer chromatography of the crude product mixture showed a complete conversion to the desired product with only minor traces of byproducts (baseline+$R_f$=0.28). This reaction was repeated 5 times on various scales and concentrations (<0.25 M) with consistent success.

EXAMPLE 7b

Saponification of the Iminoester

The crude imino ester (141 g; 0.55 mole; Example 7) was dissolved in ethanol (800 mL) in a 5 L flask equipped with a thermocouple, stirrer and addition funnel. An aqueous solution of sodium hydroxide (2 N, 325 mL, 0.63 mole) was slowly added over a period of 20 minutes while keeping the temperature below 30° C. The mixture (pH ~14) was stirred at room temperature for 1 hour until TLC (3:2::ethyl acetate:hexane) showed consumption of the ester ($R_f$=0.3) to give a new baseline material. The mixture was diluted with water (500 mL) and extracted with toluene to remove the minor organic impurities. The aqueous layer was cooled to 0° C. and slowly neutralized (pH 6.5–7) with hydrochloric acid (55 mL, 2 N). The water was evaporated under vacuum (<30° C.) to afford a crude mixture of the desired imino acid and inorganic salts as a dark wet oil (156 g). Subsequent trials indicated that the reaction mixture does not need to be diluted with water before extraction with an organic solvent. On several smaller scale attempts, the resulting crude product residue was an off-white solid and not a dark oil, the latter being caused by some impurity carried from the olefinic alcohol.

EXAMPLE 7c

Condensation/Cyclization to the Enamide

Toluene (3.5 L) was added to the oil of Example 7b. The solution was refluxed for two hours with 45 mL of residual water removed azeotropically with a Dean-Stark trap. Acetic acid (20 mL) was added and the reflux continued for 16 hours. Acetic acid catalyzed the condensation which was shown to require only 10 hours with acid catalyst, in contrast to the 60 hours necessary without acetic acid on a small scale (14 g). TLC showed a complete conversion to the desired enamide with a minor amount of unreacted baseline material. Celite (200 g) and coarse silica gel (150 g) were added to the mixture. After stirring 30 minutes, the suspension was filtered, the cake washed with toluene (3 L) and the filtrate concentrated under vacuum. The crude product (92 g; 80%) was dissolved in anhydrous THF and pushed to the next step without further purification. An alternative (and preferable) work up after acid catalysis includes filtering the inorganic salts from the toluene solution and taking the solution onto the next step.

EXAMPLE 7d

Swainsonine Acetonide

The crude enamide recovered above (90 g; 0.43 mole) was dissolved in anhydrous THF (500 mL), the solution was cooled to 0° C. and treated slowly with 1.0 M $BH_3$ in THF (1650 mL) and then left to reach room temperature while stirring overnight. By TLC (EtOAc) a new product travelled with the solvent front without traces of starting material. The solvent was removed from the clear solution under vacuum. Ethanol (1800 mL) was added followed by NaOH (64 g; 1.4 mole) and 30% hydrogen peroxide (180 mL). The mixture was refluxed for 2 hours. Thin layer chromatography (EtOAc) showed a complete conversion of the enamide ($R_f$=0.7) to the desired swainsonine acetonide ($R_f$=0.3). Baseline impurities present in the enamide preparation were carried through without any observable change in their amounts or mobility.

The solution was saturated with solid NaCl, and then extracted with ethyl acetate (5×350 mL). The organic extracts were dried over $MgSO_4$, filtered, and concentrated under vacuum to yield an off-white solid (48 g; 41%—4 steps overall from the azide). This material was crystallized from TBME to yield 18.6 g of pure product as small white needles. The mother liquor was evaporated and the residue dissolved in hot ethyl acetate and treated with warm hexane. The solution was seeded and yielded an additional 14.8 g of pure product after cooling and filtration. The mother liquor was evaporated and chromatographed to yield an additional 7.4 g of pure product (40.8 g total purified).

EXAMPLE 7e

Conversion of the Iminoester to Swainsonine Acetonide

The imino ester (13.1 g; 51.3 mmole, est. 95% pure) was dissolved in ethanol (50 mL). Sodium hydroxide (2 N, 35 mL, 68 mmole) was slowly added over a period of 20 minutes while keeping the temperature below 30° C. The mixture was stirred at room temperature for 20 hours. Thin layer chromatography (3:2::ethyl acetate:hexane) showed consumption of the ester ($R_f$=0.3) to give a new baseline material.

The mixture was cooled to 0° C. and adjusted to pH 6.0 with 2 N HCl. The ethanol was removed by rotary evaporation (water aspiration; <30° C.) and the water removed by lyophilization to afford a crude mixture of the desired imino acid and inorganic salts as an off-white solid. This crude material, dry toluene (300 mL) and glacial acetic acid (3 mL; 1 equiv) were refluxed under an argon atmosphere for 24 hours or overnight. The water produced by the condensation reaction was removed using a Dean Stark trap. Thin layer chromatography (5% MeOH in EtOAc) indicated the consumption of the imino acid to the desired enamide ($R_f$=0.7). The lightly colored toluene solution was filtered through a glass fiber filter (to remove suspended NaCl) and concentrated to 200 mL to ensure dryness of the solution and remove any traces of remaining acetic acid which may not have been collected in the Dean-Stark trap. The resulting solution was shown not to contain any significant quantities of acid and was used as is for the next step.

Under an argon atmosphere, the enamide/toluene solution was cooled to 0° C. and treated dropwise with $BH_3$ (THF (150 mL; 1M in THF). The solution was allowed to warm to room temperature while stirring overnight (~18 hrs.). The resulting solution was evaporated to dryness to give a light yellow oil. The oil was taken up in ethanol (180 mL) and treated with NaOH (7.2 g; 0.18 mole) followed by 30% $H_2O_2$ (22 mL). This mixture was refluxed for 3 hours and the solvent mixture evaporated. Brine (30 mL) was added and the product extracted with EtOAc (5×50 mL). The combined organic extracts were dried over $MgSO_4$, filtered and evaporated to give 7.58 g (69% from crude imino ester, 3 steps) of crude swainsonine acetonide as an off-white crystalline solid. The swainsonine acetonide was recrystallized from ethyl acetate/hexanes to yield 5.5 g (50%).

EXAMPLE 8

Alternate Preparation of Swainsonine Acetonide from the Olefinic Azide (Scheme VII)

Scheme VII

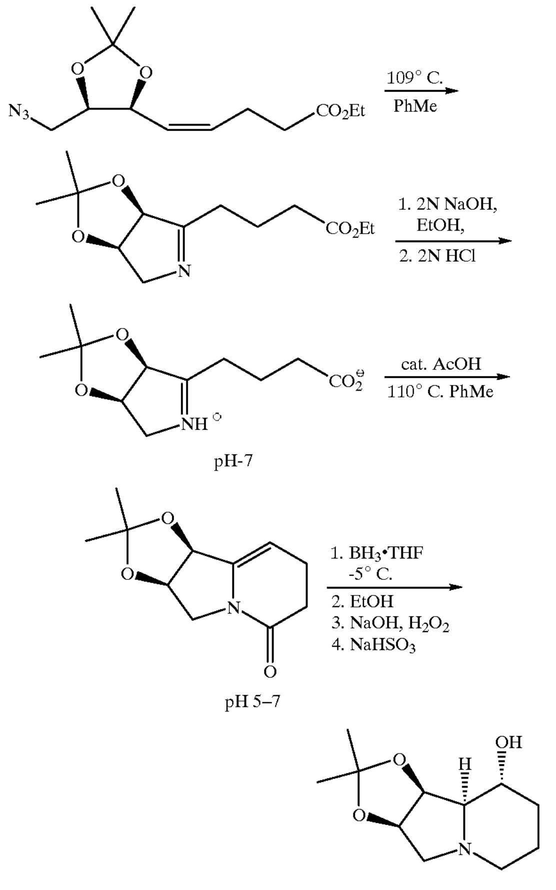

The olefinic azide [1131 g (3.99 mol)] was taken up in 28 L toluene (0.14 molar in azide) and stirred at 106° C. for 48 hours. TLC analysis showed that cyclization to the imine, was complete. Toluene was removed via vacuum distillation. The imine was taken up in 5.7 L ethanol and 2.0 L (4 mol, 1.02 equiv) of 2 N NaOH. After complete saponification (final pH=11), as determined by TLC, the reaction was neutralized with 400 mL of 2N HCl (0.8 mol) to pH 6 and left at room temperature overnight. Evaporation by vacuum distillation afforded an oily residue. The residue was taken up in 23 L of toluene and the reactor fitted with a condenser and Dean Stark trap. Residual ethanol and water were removed as a toluene azeotrope. Acetic acid (230 mL, ~1% v/v of total) was then added and ring closure to the enamide was 90% complete within 2 hrs as judged by TLC. The reaction was stirred at reflux overnight. Water and acetic acid were co-distilled as azeotropes. The distillate had a pH of 2 while the solution was pH 5–6 (moistened test strip). After cooling, the mixture was washed with 4 L water. The organic phase was dried over magnesium sulfate (1 kg) and easily filtered through an in-line glass fritted filter packed with Celite into a 72 L flask filled with an argon atmosphere. The filter was rinsed with approximately 1500 mL of toluene. The reaction mixture was cooled to 0° C. While maintaining the reaction temperature at ≦−10° C., borane-THF complex (13.6 L of 1M in THF, Aldrich, 13.6 mol, 3.4 equiv borane) was slowly added. The reaction mixture was allowed to warm to approximately 10° C. overnight. Next morning, ethanol (2.8 L) was added (with cooling) at a rate to maintain reaction mixture ≦10° C. The solution was then concentrated by vacuum distillation and the resulting residue was dissolved in THF (17 L). NaOH (1.7 L of 6N) was slowly added to the THF solution followed by the addition of 1.7 L of 30% hydrogen peroxide at a rate such that the temperature was kept below 35° C. The resulting solution was then heated to 63° C. for approximately 1.5 hours and then cooled to 30° C. Residual peroxides were quenched with solid $NaHSO_3$ (182 g). The resulting mixture was then saturated with solid NaCl (732 g). The resulting biphasic mixture was transferred to a separatory funnel. The organic phase was removed and the aqueous phase was washed three times with 1–2 liters of toluene. The combined organic phases were concentrated by vacuum distillation and dried for 3 days under high vacuum to yield 377.8 g of waxy off white solid. The residue was dissolved in 334 mL of hot ethyl acetate and filtered through a heated filter funnel. The filtrate was allowed to cool to ambient temperature overnight. The crystallized swainsonine acetonide product was collected by filtration, rinsed with cold ethyl acetate: hexanes mixture (3×50 mL) to afford an initial crop of crystals which was dried under vacuum for 3 hours (yield 233.8 g). The washes and mother liquor were combined and diluted with 100 mL of ethyl acetate. The resulting mixture was purified by silica gel chromatography using a Biotage Flash 150 L MPLC system and eluting progressively with 60:40 to 90:10 hexane:ethyl acetate. Column fractions containing product (TLC) were concentrated by vacuum distillation to afford a 25.4 grams of a white solid. This material was dissolved in 50 mL of hot ethyl acetate, to which 70 mL of hexanes was added. After cooling to ambient temperature, the resulting crystalline material was collected by vacuum filtration, rinsed twice with 50 mL of a 50:50 ethyl acetate hexane mixture, and dried under vacuum to afford 16.9 g of a second crop of swainsonine acetonide. The combined yield of both crops was 250.7 g, 1.17 mol, 29.3% yield from swainsonine acetonide. Both crops were >98% pure by $^1$H-NMR.

EXAMPLE 9

Acetonide Hydrolysis

Swainsonine acetonide (31g; 0.145 mole) was dissolved in isopropanol (300 mL). Acid (6N HCl; 300 mL) was added and the solution was stirred overnight at room temperature. Thin layer chromatography indicated that some (~20% )

acetonide was unreacted. The solvent, including the acetone byproduct and HCl, was evaporated under vacuum (40–50° C.) to drive the reaction to completion. The glassy solid was dissolved in hot isopropanol (150 mL) and allowed to sit while the product crystallized. Filtration of the yellow solution gave the final product (28 g; 91%) as a white crystalline solid after drying under vacuum (50° C.) overnight. The melting point was determined to be 189–190° C. The hydrolysis reaction was monitored by TLC 7:2:1::EtOAc:MeOH:NH4OH. Plate visualization was best achieved with iodine. The $R_f$ values for swainsonine and the acetonide were 0.29 and 0.73, respectively.

Removing all traces of water is important to ensure a good crystallization yield. Starting with slightly impure acetonide resulted in dark coloration (brown to red to black in some cases) and decreased crystallization yield. Crystals thus obtained should be recrystallized. Swainsonine hydrochloride is practically insoluble in isopropanol. Recrystallization can be achieved from a saturated boiling ethanol (denatured) solution or from methanol/ether by dissolving in a minimum of methanol (~10% w/v), filtering and then slowly adding an equivalent amount of diethyl ether (clear prisms; 75–80% recovery). HPLC protocol for determining purity Column: 4.6×250 mm, 0.5 cm, Phenomenex, Prodigy 5 ODS-2

Solvent: 5% acetonitrile /95% aqueous $KH_2PO_4$ (pH 9.0), 1 mL/min

Detection: UV, 205 nm

Retention time: 5.5 minutes

EXAMPLE 10

Deacetonation Reaction

Swainsonine acetonide (237.4 g, 1.11 mol) was dissolved in 2-propanol (2.47 L) with stirring in a 22 L flask fitted with a mechanical stirrer, condenser, thermocouple, and heating/cooling bath. The vessel was chilled to 7° C. and a chilled 6 N HCl solution (1.24 L) was added slowly via an addition funnel with stirring. The resulting mixture was allowed to warm to ambient temperature (19° C.) with stirring overnight (15 hours). TLC showed the reaction to be 90% complete. The volume was concentrated to about 1.3 L by vacuum distillation (pot temperature 22 to 35° C. at 20 to 25 torr, 3.6 L distillate collected). Water was then removed by repeatedly adding 2-propanol and distilling solvent.

| 2-propanol added | distillate collected | temperature | pressure | precipitate observed |
|---|---|---|---|---|
| 3.7 L | 3.9 L | 22 to 33° C. | 20–40 torr | no |
| 3.9 L | 3.8 L | 19 to 25° C. | 20–40 torr | no |
| 3.8 L | 1.4 L | <40° C. | N/A | yes |
| 2.0 L | 2.0 L | 21 to 24° C. | 20 torr | yes |

The reaction mixture was cooled to 19° C. and the product collected by filtering through an in-line coarse-fritted glass filtration unit. The filter cake was rinsed with 500 mL chilled (10 to 15° C.) 2-propanol. The filter unit was sealed off and evacuated (20 down to 1 torr over 4 days) in order to dry the product to a constant weight. The flaky white product was transferred to brown glass bottles and stored under an Argon atmosphere. Samples were sent for NMR and assay. Yield=217.2 g (89%). Melting point=188–190° C.

The crystalline product has the properties reported in PCT/CA98/00360. In particular, (−)-(1S, 2S,8R,8aR)-1,2,8-trihydroxyoctahydro-indolizidine hydrochloride salt (swainsonine hydrochloride), was a white to off-white crystalline solid, molecular weight 209.67,and pKa 7.4.

EXAMPLE 11

Alternative Route to Isopropylidene Erythronolactone

Potassium erythronate (Pfanstiehl Laboratories, Waukegan, Ill.) (2.0 g, 11.5 mmole) was briefly stirred in 50 ml hot reagent grade acetone (50–55° C.). After adding p-toluenesulfonic acid (2.3 g), the solution was refluxed for 1.5 hours. The solution was cooled, and the insoluble potassium tosylate and unreacted potassium erythronate were removed by filtration. The filtrate was concentrated to remove water, and the redissolved in 50 ml acetone. Anhydrous magnesium sulfate (2.5 g) was added and the pH was adjusted to 5.5 with p-toluenesulfonic acid. After refluxing for 1.5 hours, TLC and GC-MS indicated a thorough conversion, the solution was cooled to room temperature, solids were removed by filtration, and the filtrate was adjusted to pH 7.0 with a small amount of triethyl amine. After concentration, the residue was redissolved in a minimum of t-butyl methyl ether. Hexane was added until the solution became turbid. After standing for 30 minues, the cottony solid was filtered and dried under vacuum to yield 1.1 g (60%). No attempt was made to recover more product from the mother liquor.

EXAMPLE 12

Alternative Route to Isopropylidene Erythronolactone

This example was identical to Example 11, except after the first evaporation of acetone to remove water, 30 ml toluene was added and evaporated to remove additional water, before redissolving in 50 ml acetone. The isolated yield was 1.0 g (56%).

This reaction can be improved by, for example, using more p-toluene sulfonic acid (pTSA or another protonic acid such as sulfuric acid) to establish a pH lower than 5.5 (such as between 1.0 and 5.0, or between 2.5 and 4.0); refluxing in acetone longer than 1.5 hours; replacing neutralization of pTSA with base such as triethyl amine with a work-up which includes solid sodium bicarbonate and filtration; or adding a little water during the acetonation process to improve solubility. The additional water can be coevaporated with acetone or removed with magnesium sulfate.

OTHER EMBODIMENTS

Based on the examples and description above, a person of ordinary skill in the art of the invention would easily recognize the essential features of the invention and, without going beyond the spirit and scope thereof, be able to adapt the invention to various usages and conditions.

In particular, variations and substitutions in the above synthetic transformations will be apparent to those of skill in organic chemistry.

All publications, patents and patent applications are herein incorporated by reference in their entirety to the same extent as if each individual publication, patent or patent application was specifically and individually indicated to be incorporated by reference in its entirety.

We claim:

1. A method for synthesizing a salt of swainsonine comprising (i) subjecting a compound of the formula I

I

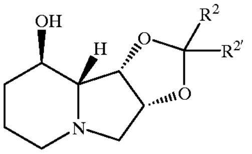

wherein $R^2$ and $R^{2'}$ are the same or different and represent alkyl, halogen, alkenyl, alkoxy, cycloalkyl or aryl, to acid hydrolysis in the presence of a $C_{1-4}$ alkanol to obtain a crystalline salt of swainsonine; and optionally (ii) recrystallizing the swainsonine salt from a $C_{1-4}$ alkanol.

2. A method as claimed in claim 1 wherein $R^2$ and $R^{2'}$ are the same and represent $C_{1-4}$ alkyl.

3. A method as claimed in claim 1 wherein one of $R^2$ and $R^{2'}$ represents alkyl or aryl and the other of $R^2$ and $R^{2'}$ represents alkoxy or halogen.

4. A method as claimed in claim 1 wherein the compound of the formula I is 1,2-O-isopropylidenedioxy-8-hydroxyindolizidine.

5. A method of claim 1 for preparing an isolated and purified crystalline hydrochloride salt of swainsonine comprising converting 1,2-O-isopropylidenedioxy-8-hydroxyindolizidine to a hydrochloride salt by acid hydrolysis in the presence of a $C_{1-4}$ alkanol to obtain a crystalline hydrochloride salt of swainsonine, and optionally recrystallizing the salt in a $C_{1-4}$ alkanol.

6. A method as claimed in claim 1 wherein the acid hydrolysis includes hydrochloric acid.

7. A method as claimed in claim 1 wherein the acid hydrolysis includes hydrogen fluoride or hydrogen bromide.

8. A method for preparing a salts of swainsonine of claim 1

(i) cyclizing an amino acid of the formula VII

VII

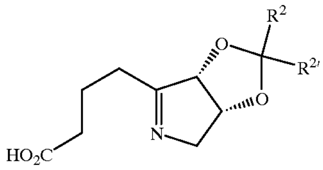

wherein $R^2$ and $R^{2'}$ are the same or different and represent alkyl, halogen, alkenyl, alkoxy, cycloalkyl or aryl by refluxing in an organic solvent with a catalyst, to form a compound of the formula VIII;

VIII

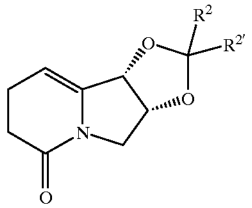

wherein $R^2$ and $R^{2'}$ are as defined above (ii) reducing the enamide of the formula VIII with a borane reagent in an organic solvent, and oxidizing by peroxide the resulting alkyl borane, to obtain a protected swainsonine of the formula I;

I

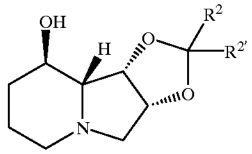

wherein $R^2$ and $R^{2'}$ are as defined above;

(iii) subjecting the protected swainsonine to acid hydrolysis in the presence of a $C_{1-4}$ alkanol to obtain a crystalline swainsonine salt; and optionally (iv) recrystallizing the swainsonine salt from a $C_{1-4}$ alkanol.

9. A method for preparing a salt of swainsonine of claim 1 comprising:

(i) reacting an olefinic alcohol of the formula IV

IV

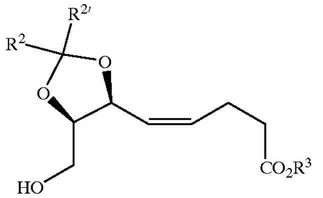

wherein $R^2$ and $R^{2'}$ are the same or different and represent alkyl, halogen, alkenyl, alkoxy, cyloalkyl or aryl, and $R^3$ is $C_{1-10}$ alkyl or aryl, with a phosphine, dialkylazodicarboxylate, and azide source to obtain an azide of the formula V

V

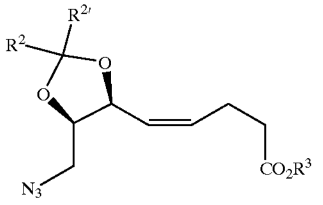

wherein $R^2$, $R^{2'}$, and $R^3$ are as defined above;

(ii) refluxing the azide of the formula V in a non-reactive high boiling solvent to form an amino ester of the formula VI

VI

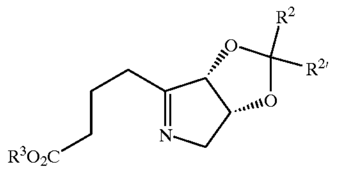

wherein $R^2$, $R^{2'}$, and $R^3$ are as defined above;

(iii) reacting the imino ester of the formula VI with an alkali metal hydroxide in a mixture of water and a miscible non-reactive organic solvent and acidifying the reaction mixture to obtain an imino acid of the formula VII

VII

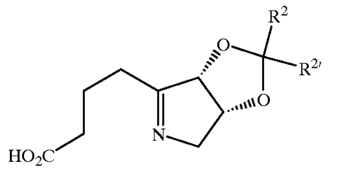

wherein $R^2$ and $R^{2'}$ are as defined above;

(ii) cyclizing the imino acid of the formula VI by refluxing in an organic solvent with a catalyst, to form an enamide of the formula VIII;

VIII

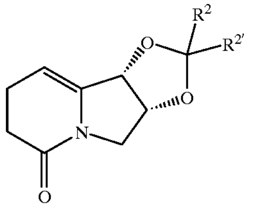

wherein $R^2$ and $R^{2'}$ are as defined above (v) reducing the enamide of the formula VIII with a borane reagent in an organic solvent and oxidizing by peroxide the resulting alkyl borane, to obtain a protected swainsonine of the formula I

I

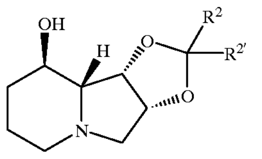

wherein $R^2$ and $R^{2'}$ are as defined above;

(vi) subjecting the protected swainsonine to acid hydrolysis in the presence of a $C_{1-4}$ alkanol to obtain a crystalline swainsonine salt; and optionally (vii) recrystallizing the swainsonine salt from a $C_{1-4}$ alkanol.

10. A method for preparing a salt of swainsonine of claim 1 comprising:

(A) reacting a lactone of the formula II

II

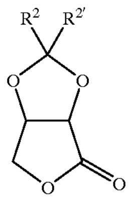

wherein $R^2$ and $R^{2'}$ are the same or different and represent alkyl, alkenyl, halogen, alkoxy, cycloalkyl, or aryl, with diisobutylalumnium hydride in an organic solvent to obtain a lactol of the formula III

III

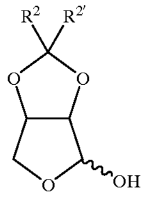

wherein $R^2$ and $R^{2'}$ are as defined above;

(B) reacting the lactol of the formula III with a phosphonium bromide salt to obtain an olefinic alcohol of the formula IV:

IV

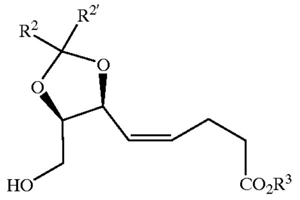

wherein $R^2$ and $R^{2'}$ are as defined above, and $R^3$ is $C_{1-10}$ alkyl or aryl;

(C) reacting the olefinic alcohol of the formula IV with a phosphine, dialkylazodicarboxylate, and azide source to obtain an azide of the formula V

V

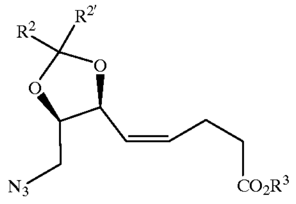

wherein $R^2$, $R^{2'}$, and $R^3$ are as defined above;

(D) refluxing the azide of the formula V in a non-reactive high boiling solvent to form an imino ester of the formula VI

VI

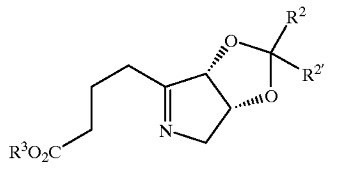

wherein $R^2$, $R^{2'}$ and $R^3$ are as defined above;

(E) reacting the imino ester of the formula VI with an alkali metal hydroxide in a mixture of water and a miscible non-reactive organic solvent and acidifying the reaction mixture to obtain an imino acid of the formula VII

VII

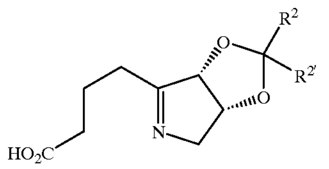

wherein $R^2$ and $R^{2'}$ are defined above;

(F) cyclizing the imino acid of the formula VII by refluxing in an organic solvent, with a catalyst, to form an enamide of the formula VIII;

VIII

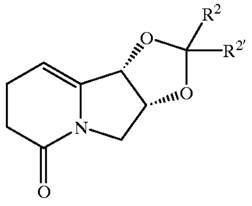

wherein $R^2$ and $R^{2'}$ are as defined above (G) reducing the enamide of the formula VIII with a borane reagent in an organic solvent and oxidizing by peroxide the resulting alkyl borane, to obtain a protected swainsonine of the formula I;

I

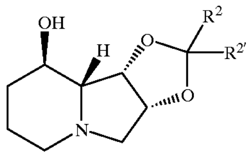

wherein $R^2$ and $R^{2'}$ are as defined above;

(H) subjecting the protected swainsonine to acid hydrolysis in the presence of a $C_{1-4}$ alkanol to obtain a crystalline swainsonine salt; and optionally (I) recrystallizing the swainsonine salt from a $C_{1-4}$ alkanol.

11. A method for preparing a compound of the formula V

V

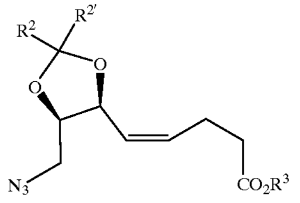

wherein $R^2$ and $R^{2'}$ are the same or different and represent alkyl, halogen, alkenyl, alkoxy, cycloalkyl or aryl, and $R^3$ is $C_{1-10}$ alkyl or aryl, comprising reacting an olefinic alcohol of the formula IV

IV

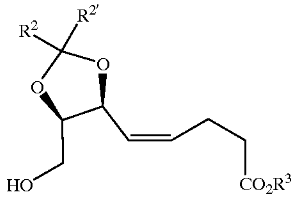

wherein $R^2$, $R^{2'}$, and $R^3$ are a defined above, with a phosphine, dialkylazodicarboxylate, and azide source to obtain a compound of the formula V.

12. A method for synthesizing swainsonine salts, said method comprising the steps:

(H)(i) converting in alkylidene-protected swainsonine to the swainsonine salt by acid hydrolysis in the presence of a $C_{1-3}$ alkanol solvent at room temperature; and (H)(ii) recrystallizing the swainsonine salt from a $C_{1-3}$ alkanol solvent.

13. A method of claim 12, further comprising before said step (H) the step (F) cyclizing an imino acid (−)-(1S,5R)-3,3-dialkyl-8-(3-carboxy-1-propyl)-7-aza-2,4-dioxabicyclo[3.3.0]oct-7-ene by refluxing in toluene with a catalytic amount of a lower alkyl carboxylic acid to form an enamide.

14. A method of claim 12, further comprising before said step (H) the steps:

(C)(i) reacting the olefinic alcohol (+)-(4R,cis)(Z)-2,2-dialkyl-5-(4-carbethoxy-1-butenyl)-1,3-dioxolane-4-methanol with a molar equivalent of triphenyl phosphine in THF, a molar equivalent of diisopropylazodicarboxylate, and trimethylsilyl azide;

(C)(ii) adding tetrabutylammonium fluoride in THF to the azide; and (C)(iii) repeating steps (C)(i) and (C)(ii) with the reaction product mixture of (C)(ii) to form the azide product.

15. A method of claim 12, further comprising before said step (H), the steps:

(a) reacting D-isoascorbic acid with aqueous sodium bicarbonate and hydrogen peroxide;

(b) neutralizing excess carbonate with a protonic acid to a pH between 3.5 and 4.2;

(c) reacting the crude erythronolactone with a catalytic sulfonic acid in acetone and magnesium sulfate; and (d) crystallizing 2,3-O-alkylidene erythronolactone from ether/hexanes or t-butyl methyl ether/hexane.

16. A method of claim 12, further comprising before said step (H) the steps:

(C)(i) reacting the olefinic alcohol with a molar equivalent of triphenyl phosphine in THF, followed by a molar equivalent of diisopropylazodicarboxylate, and then trimethylsilyl azide;

(C)(ii) adding tetrabutylammonium fluoride in THF; and (C)(iii) repeating steps (C)(i) and (C)(ii) with the reaction product mixture of step (C)(ii) to form the azide product;

(D) refluxing said azide after purification, in toluene at an initial concentration of between 0.30 and 0.05 M to form the imino ester;

(E) reacting said imino ester with a molar excess of an alkali metal hydroxide in a mixture of water and ethanol and then acidifying the reaction mixture to about pH 6–7 to yield the imino acid;

(F) cyclizing said imino acid by refluxing in toluene with a catalytic amount of a lower alkyl carboxylic acid to form the enamide; and (G) reducing said enamide with diborane-THF in toluene, and crystallizing the crude solid in t-butyl methyl ether or in ethyl acetate/hexane.

17. A method of claim 12, further comprising before step (H), the step (e) of preparing 2,3-O-isopropylidene erythronolactone from potassium erythronate and acetone with catalytic acid.

18. A method as claimed in claim 1, wherein the acid used during acid hydrolysis includes hydrofluoric acid, hydrobromic acid, or hydrogen chloride.

19. A method as claimed in claim 1, wherein the $C_{1-4}$ alkanol is methanol, ethanol, propanol, isopropanol, or butanol.

20. A method as claimed in claim 1, wherein the method is carried out at a temperature of 0° C.–25° C.

21. A method as claimed in claim 8, wherein in step (i) the organic solvent is toluene, benzene, xylene, chlorobenzene, or t-butyl methyl ether and the catalyst is a Lewis acid.

22. A method as claimed in claim 21, wherein the catalyst is a carboxylic acid or sulfonic acid.

23. A method as claimed in claim 21, wherein the catalyst is formic acid, acetic acid, trifluoroacetic acid, propionic acid, butyric acid, trichloroacetic acid, toluene sulfonic acid, camphor sulfonic acid, sulfuric acid, methane sulfonic acid, benzoic acid, or HCl gas.

24. A method as claimed in claim 8, wherein in step (ii) the borane reagent is borane-THF complex, borane dimethyl sulfide complex, or a mono- or disubstituted borane and the organic solvent is toluene, THF, benzene, xylene, chlorobenzene, blends of petroleum ether, ether, t-butyl methyl ether ethylformate, ethyl acetate/hexane, ethyl acetate/petroleum ether, or ethyl acetate/heptane.

25. A method as claimed in claim 8, wherein in step (iii) the acid used during acid hydrolysis includes hydrochloric acid, hydrofluoric acid, hydrobromic acid, hydrogen fluoride, hydrogen chloride, or hydrogen bromide, and the $C_{1-4}$ alkanol is methanol, ethanol, propanol, isopropanol, or butanol.

26. A method as claimed in claim 9, wherein in step (i) the phosphine is a trialkyl phosphine or a triaryl phosphine.

27. A method as claimed in claim 26, wherein the phosphine is trimethylphosphine, triphenylphosphine, tribenzyl phosphine, or paramethylphenyl phosphine.

28. A method as claimed in claim 9, wherein in step (i) the dialkylazodicarboxylate is diethylazodicarboxylate (DEAD), dimethylazodicarboxylate, dibutylazodicarboxylate, or diisopropylazodicarboxylate (DIAD), and the azide source is azido trimethylsilane (TMS-$N_3$), diphenylphosphorylazide, tetrabutylammonium azide, or hydrazoic acid.

29. A method as claimed in claim 9, wherein in step (i) one or more of a Crown ether, metal azide or tetrabutyl ammonium fluoride are present.

30. A method as claimed in claim 9, wherein in step (ii) the non-reactive high boiling solvent is toluene, benzene, xylene, chlorobenzene, or dimethyl formamide.

31. A method as claimed in claim 9, wherein in step (iii) the alkali metal hydroxide is NaOH, LiOH, or KOH and the miscible non-reactive organic solvent is a $C_{1-4}$ alkanol.

32. A method as claimed in claim 9, wherein in step (iv) the organic solvent is toluene, benzene, xylene, chlorobenzene, or t-butyl methyl ether, and the catalyst is a Lewis acid.

33. A method as claimed in claim 32, wherein the catalyst is a carboxylic acid or sulfonic acid.

34. A method as claimed in claim 33, wherein the catalyst is formic acid, acetic acid, trifluoroacetic acid, propionic acid, butyric acid, trichloroacetic acid, toluene sulfonic acid, camphor sulfonic acid, sulfuric acid, methane sulfonic acid, benzoic acid, or HCl gas.

35. A method as claimed in claim 9, wherein in step (v) the borane reagent is borane-THF complex, borane dimethyl sulfide complex, or a mono- or disubstituted borane such as methyl- or dimethyl thexyl, 9-BBN, or monochloroborane, and the organic solvent is toluene, THF, benzene, xylene, chlorobenzene, blends of petroleum ether, ether, t-butyl methyl ether ethylformate, ethyl acetate/hexane, ethyl acetate/petroleum ether, or ethyl acetate/heptane.

36. A method as claimed in claim 9, wherein in step (vi) the acid used during acid hydrolysis includes hydrochloric acid, hydrofluoric acid, hydrobromic acid, hydrogen fluoride, hydrogen chloride, or hydrogen bromide, and the $C_{1-4}$ alkanol is methanol, ethanol, propanol, isopropanol, or butanol.

37. A method as claimed in claim 10, wherein in Step (A) the organic solvent is toluene, benzene, xylene, chlorobenzene, or t-butyl methyl ether.

38. A method as claimed in claim 10, wherein in Step (A) NaCl or NaOH are added to the reaction mixture.

39. A method as claimed in claim 10, wherein in Step (B) the phosphonium bromide salt is ethyl 4-triphenylphosphonium butyrate bromide salt.

40. A method as claimed in claim 10, wherein in Step (C) the phosphine is a trialkylphosphine or a triaryl phosphine.

41. A method as claimed in claim 40, wherein the phosphine is trimethylphosphine, triphenylphosphine, tribenzyl phosphine, or paramethylphenyl phosphine.

42. A method as claimed in claim 10, wherein in Step (C) the azide source is azido trimethylsilane (TMS-$N_3$), diphenylphosphorylazide, tetrabutylammonium azide, or hydrazoic acid and the dialkylazodicarboxylate is diethylazodicarboxylate (DEAD), dimethylazodicarboxylate, dibutylazodicarboxylate, or diisopropylazodicarboxylate (DIAD).

43. A method as claimed in claim 10, wherein in Step (D) the non-reactive high boiling solvent is toluene, benzene, xylene, chlorobenzene, or dimethyl formamide.

44. A method as claimed in claim 10, wherein in Step (E) the alkali metal hydroxide is NaOH, LiOH, or KOH, and the miscible non-reactive organic solvent is a $C_{1-4}$ alkanol.

45. A method as claimed in claim 10, wherein in Step (F) the organic solvent is toluene, benzene, xylene, chlorobenzene, or t-butyl methyl ether, and the catalyst is a Lewis acid.

46. A method as claimed in claim 10, wherein in Step (G) the borane reagent is borane-THF complex, borane dimethyl sulfide complex, or a mono- or disubstituted borane such as methyl- or dimethyl thexyl, 9-BBN, or monochloroborane.

47. A method as claimed in claim 10, wherein in Step (G) the organic solvent is toluene, THF, benzene, xylene, chlorobenzene, blends of petroleum ether, ether, t-butyl methyl ether ethylformate, ethyl acetate/hexane, ethyl acetate/petroleum ether, or ethyl acetate/heptane.

48. A method as claimed in claim 11, wherein the phosphine is a trialkyl phosphine or a triaryl phosphine.

49. A method as claimed in claim 48, wherein the phosphine is trimethylphosphine, triphenylphosphine, tribenzyl phosphine, or paramethylphenyl phosphine.

50. A method as claimed in claim 11, wherein the dialkylazodicarboxylate is diethylazodicarboxylate (DEAD), dimethylazodicarboxylate, dibutylazodicarboxylate, or diisopropylazodicarboxylate (DIAD).

51. A method as claimed in claim 11, wherein the azide source is azido trimethylsilane (TMS-$N_3$), diphenylphosphorylazide, tetrabutylammonium azide, or hydrazoic acid.

52. A method as claimed in claim 12, wherein the $C_{1-3}$ alkanol is methanol, ethanol, propanol, or isopropanol.

53. A method as claimed in claim 12, wherein the acid used during acid hydrolysis includes hydrochloric acid, hydrofluoric acid, hydrobromic acid, hydrogen fluoride, hydrogen chloride, or hydrogen bromide.

* * * * *